US008425917B2

(12) United States Patent
Hirst

(10) Patent No.: US 8,425,917 B2
(45) Date of Patent: *Apr. 23, 2013

(54) MUTANT FORMS OF ETXB AND CTXB AND THEIR USE AS CARRIERS

(75) Inventor: Timothy Raymond Hirst, Forrest (AU)

(73) Assignee: Hunter Immunology Ltd (AU)

( * ) Notice: Subject to any disclaimer, the term of this patent is extended or adjusted under 35 U.S.C. 154(b) by 1393 days.

This patent is subject to a terminal disclaimer.

(21) Appl. No.: 12/112,952

(22) Filed: Apr. 30, 2008

(65) Prior Publication Data

US 2008/0305125 A1 Dec. 11, 2008

Related U.S. Application Data

(63) Continuation of application No. 10/743,391, filed on Dec. 22, 2003, now Pat. No. 7,422,752, which is a continuation of application No. PCT/GB02/02829, filed on Jun. 20, 2002.

(30) Foreign Application Priority Data

Jun. 22, 2001 (GB) .................................. 0115382.4

(51) Int. Cl.
*A61K 39/108* (2006.01)
*A61K 39/106* (2006.01)
*A01N 37/18* (2006.01)

(52) U.S. Cl.
USPC .................. 424/241.1; 424/257.1; 424/261.1; 514/2

(58) Field of Classification Search .................. None
See application file for complete search history.

(56) References Cited

FOREIGN PATENT DOCUMENTS

| WO | WO 97/02045 | 1/1997 |
| WO | WO 99/58145 | 11/1999 |
| WO | WO 00/14114 | 3/2000 |
| WO | WO 01/27144 | 4/2001 |

OTHER PUBLICATIONS

Bowie et al (Science, 1990, 257:1306-1310).*
Bork (Genome Research, 2000,10:398-400).*
Bergerot, et al., A Cholera Toxoid-Insulin Conjugate as an Oral Vaccine Against Spontaneous Autoimmune Diabetes, Proceedings of the National Academy of Sciences, Apr. 1997, 4610-4614, vol. 94.
Sun, et al., Treatment of Experimental Autoimmune Encephalomyelitis by Feeding Myelin Basic Protein Conjugated to Cholera Toxin B Subunit, Proceedings of the National Academy of Sciences, Jul. 1996, 7196-7201, vol. 93.
Plant et al., Modulation of the Immune Response by The Cholera-Like Enterotoxins, Current Topics in Medicinal Chemistry, 2004, 509-519, vol. 4.
Michl, et al., Bacteria and Bacterial Toxins as Therapeutic Agents for Solid Tumors, Current Cancer Drug Targets, 2004, 689-702, vol. 4.
Loregian, et al., Intranuclear Delivery of an Antiviral Peptide Mediated by the B Subunit of *Escherichia coli* Heat-Labile Enterotoxin, Apr. 1999, 5221-5226, vol. 96.
Nashar, et al., Current Progress in the Development of the B Subunits of Cholera Toxin and *Escherichia coli* Heat-Labile Enterotoxin As Carriers for the Oral Delivery of Heterologous Antigens and Epitopes, 1993, 235-240, vol. 11.
Marcello, et al., Specific Inhibition of Herpers Virus Replication by Receptor-Mediated Entry of an Antiviral Peptide Linked to *Escherichia coli* Enterotoxin B Subunit, Sep. 1994, 8994-8998, vol. 91.
Nashar, et al., Evidence for a Role of Ganglioside GM1 in Antigen Presentation: Binding Enhances Presentation of *Escherichia coli* Enterotoxin B Subunit (ExtB) to CD4+ T Cells, 2001, 541-551, vol. 13.

* cited by examiner

*Primary Examiner* — Robert A Zeman
(74) *Attorney, Agent, or Firm* — St. Onge Steward Johnston & Reens LLC

(57) ABSTRACT

The present invention describes the use of a mutant form of EtxB or CtxB to deliver an agent to a target cell wherein the mutant has GM-1 binding activity; but wherein the mutant has a reduced immunogenic and immunomodulatory activity relative to the wild type form of EtxB or CtxB.

12 Claims, 12 Drawing Sheets

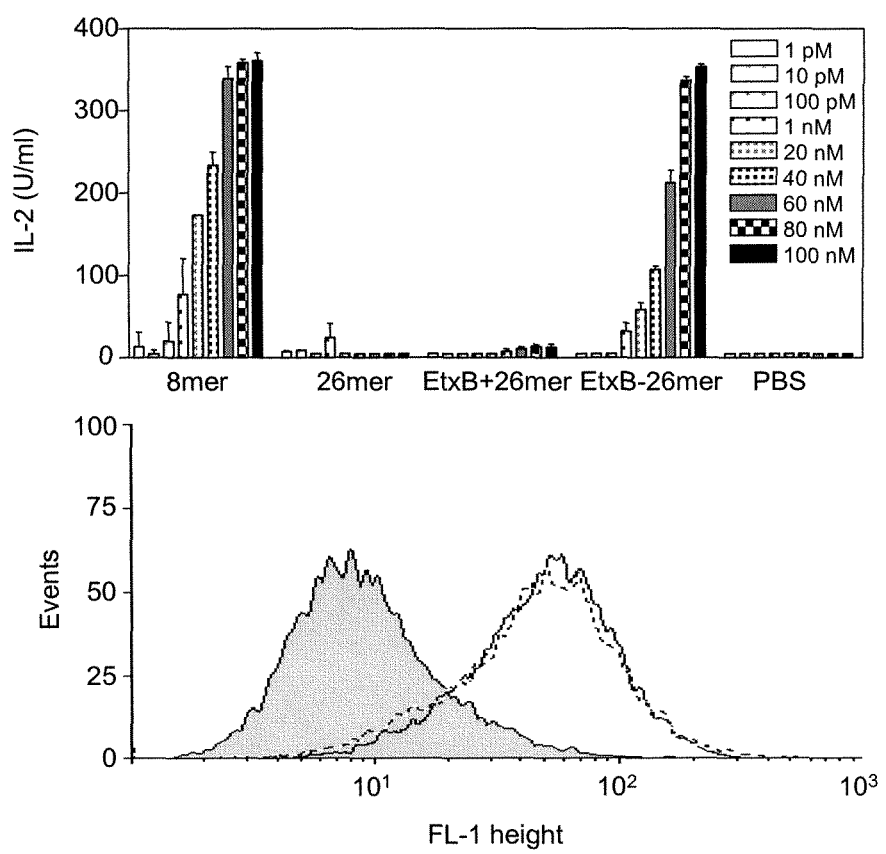

SEQUENCE LISTING

```
<160> NUMBER OF SEQ ID NOS: 19

<210> SEQ ID NO 1
<211> LENGTH: 8
<212> TYPE: PRT
<213> ORGANISM: Escherichia coli

<400> SEQUENCE: 1

Glu Val Pro Gly Ser Gln His Ile
1               5

<210> SEQ ID NO 2
<211> LENGTH: 8
<212> TYPE: PRT
<213> ORGANISM: Escherichia coli
<220> FEATURE:
<221> NAME/KEY: MUTAGEN
```

```
<222> LOCATION: (1)..(1)
<223> OTHER INFORMATION: Xaa may be any amino acid.
<220> FEATURE:
<221> NAME/KEY: MUTAGEN
<222> LOCATION: (6)..(6)
<223> OTHER INFORMATION: Xaa may be any amino acid.
<220> FEATURE:
<221> NAME/KEY: MUTAGEN
<222> LOCATION: (7)..(7)
<223> OTHER INFORMATION: Xaa may be any amino acid.

<400> SEQUENCE: 2

Xaa Val Pro Gly Ser Xaa Xaa Ile
1               5

<210> SEQ ID NO 3
<211> LENGTH: 8
<212> TYPE: PRT
<213> ORGANISM: Escherichia coli
<220> FEATURE:
<221> NAME/KEY: MUTAGEN
<222> LOCATION: (7)..(7)
<223> OTHER INFORMATION: Xaa is His, Ala or Ser

<400> SEQUENCE: 3

Glu Val Pro Gly Ser Gln Xaa Ile
1               5

<210> SEQ ID NO 4
<211> LENGTH: 8
<212> TYPE: PRT
<213> ORGANISM: Artificial
<220> FEATURE:
<223> OTHER INFORMATION: Synthetic peptide

<400> SEQUENCE: 4

Ser Ile Ile Asn Phe Glu Lys Leu
1               5

<210> SEQ ID NO 5
<211> LENGTH: 9
<212> TYPE: PRT
<213> ORGANISM: Artificial
<220> FEATURE:
<223> OTHER INFORMATION: Synthetic peptide

<400> SEQUENCE: 5

Cys Ser Ile Ile Asn Phe Glu Lys Leu
1               5

<210> SEQ ID NO 6
<211> LENGTH: 16
<212> TYPE: PRT
<213> ORGANISM: Artificial
<220> FEATURE:
<223> OTHER INFORMATION: Synthetic peptide

<400> SEQUENCE: 6

Cys Glu Lys Leu Ala Gly Phe Gly Ser Ile Ile Asn Phe Glu Lys Leu
1               5                   10                  15

<210> SEQ ID NO 7
<211> LENGTH: 19
<212> TYPE: PRT
<213> ORGANISM: Artificial
<220> FEATURE:
<223> OTHER INFORMATION: Synthetic peptide

<400> SEQUENCE: 7
```

Cys Ala Val Gly Ala Gly Ala Thr Ala Glu Glu Ser Ile Ile Asn Phe
1               5                   10                  15

Glu Lys Leu

<210> SEQ ID NO 8
<211> LENGTH: 26
<212> TYPE: PRT
<213> ORGANISM: Artificial
<220> FEATURE:
<223> OTHER INFORMATION: Synthetic peptide

<400> SEQUENCE: 8

Cys Glu Lys Leu Ala Gly Phe Gly Ala Val Gly Ala Gly Ala Thr Ala
1               5                   10                  15

Glu Glu Ser Ile Ile Asn Phe Glu Lys Leu
                20                  25

<210> SEQ ID NO 9
<211> LENGTH: 26
<212> TYPE: PRT
<213> ORGANISM: Artificial
<220> FEATURE:
<223> OTHER INFORMATION: Synthetic peptide

<400> SEQUENCE: 9

Cys Glu Lys Leu Ala Gly Phe Gly Ala Arg Gly Ala Gly Ala Thr Ala
1               5                   10                  15

Glu Glu Ser Ile Ile Asn Phe Glu Lys Leu
                20                  25

<210> SEQ ID NO 10
<211> LENGTH: 31
<212> TYPE: PRT
<213> ORGANISM: Artificial
<220> FEATURE:
<223> OTHER INFORMATION: Synthetic peptide

<400> SEQUENCE: 10

Cys Glu Lys Leu Ala Gly Phe Gly Ala Val Gly Ala Gly Ala Thr Ala
1               5                   10                  15

Glu Glu Ser Ile Ile Asn Phe Glu Lys Leu Thr Glu Trp Thr Ser
                20                  25                  30

<210> SEQ ID NO 11
<211> LENGTH: 14
<212> TYPE: PRT
<213> ORGANISM: herpes simplex virus 1

<400> SEQUENCE: 11

Ala Gly Phe Gly Ala Val Gly Ala Gly Ala Thr Ala Glu Glu
1               5                   10

<210> SEQ ID NO 12
<211> LENGTH: 103
<212> TYPE: PRT
<213> ORGANISM: Vibrio cholerae

<400> SEQUENCE: 12

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
                20                  25                  30

Gly Lys Arg Glu Met Ala Ile Ile Thr Phe Lys Asn Gly Ala Thr Phe
            35                  40                  45

-continued

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 13
<211> LENGTH: 103
<212> TYPE: PRT
<213> ORGANISM: Vibrio cholerae

<400> SEQUENCE: 13

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
                20                  25                  30

Gly Lys Arg Glu Met Ala Ile Ile Thr Phe Lys Asn Gly Ala Thr Phe
            35                  40                  45

Gln Val Glu Val Pro Gly Ser Gln Ala Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 14
<211> LENGTH: 103
<212> TYPE: PRT
<213> ORGANISM: Escherichia coli

<400> SEQUENCE: 14

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
                20                  25                  30

Asp Lys Arg Glu Met Val Ile Ile Thr Phe Lys Ser Gly Glu Thr Phe
            35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Ile Ser Ile
                85                  90                  95

Ala Ala Ile Ser Met Glu Asn
            100

<210> SEQ ID NO 15
<211> LENGTH: 103
<212> TYPE: PRT
<213> ORGANISM: Escherichia coli

<400> SEQUENCE: 15

Ala Pro Gln Thr Ile Thr Glu Leu Cys Ser Glu Tyr Arg Asn Thr Gln

-continued

```
                1               5                  10                 15
Ile Tyr Thr Ile Asn Asp Lys Ile Leu Ser Tyr Thr Glu Ser Met Ala
                20                 25                 30

Gly Lys Arg Glu Met Val Ile Ile Thr Phe Lys Ser Gly Glu Thr Phe
            35                 40                 45

Gln Val Glu Val Pro Gly Ser Gln His Ile Asp Ser Gln Lys Lys Ala
        50                 55                 60

Ile Glu Arg Met Lys Asp Thr Leu Arg Ile Thr Tyr Leu Thr Glu Thr
65                 70                 75                 80

Lys Ile Asp Lys Leu Cys Val Trp Asn Asn Lys Thr Pro Ile Ser Ile
                85                 90                 95

Ala Ala Ile Ser Met Glu Asn
            100
```

<210> SEQ ID NO 16
<211> LENGTH: 103
<212> TYPE: PRT
<213> ORGANISM: Escherichia coli

<400> SEQUENCE: 16

```
Ala Pro Gln Thr Ile Thr Glu Leu Cys Ser Glu Tyr Arg Asn Thr Gln
1               5                  10                 15

Ile Tyr Thr Ile Asn Asp Lys Ile Leu Ser Tyr Thr Glu Ser Met Ala
                20                 25                 30

Gly Lys Arg Glu Met Val Ile Ile Thr Phe Lys Ser Gly Glu Thr Phe
            35                 40                 45

Gln Val Glu Val Pro Gly Ser Gln Ala Ile Asp Ser Gln Lys Lys Ala
        50                 55                 60

Ile Glu Arg Met Lys Asp Thr Leu Arg Ile Thr Tyr Leu Thr Glu Thr
65                 70                 75                 80

Lys Ile Asp Lys Leu Cys Val Trp Asn Asn Lys Thr Pro Ile Ser Ile
                85                 90                 95

Ala Ala Ile Ser Met Glu Asn
            100
```

<210> SEQ ID NO 17
<211> LENGTH: 103
<212> TYPE: PRT
<213> ORGANISM: Vibrio cholerae

<400> SEQUENCE: 17

```
Thr Pro Gln Asn Ile Thr Asp Leu Cys Ala Glu Tyr His Asn Thr Gln
1               5                  10                 15

Ile His Thr Leu Asn Asp Lys Ile Phe Ser Tyr Thr Glu Ser Leu Ala
                20                 25                 30

Gly Lys Arg Glu Met Ala Ile Ile Thr Phe Lys Asn Gly Ala Thr Phe
            35                 40                 45

Gln Val Ala Val Pro Gly Ser Gln His Ile Asp Ser Gln Lys Lys Ala
        50                 55                 60

Ile Glu Arg Met Lys Asp Thr Leu Arg Ile Ala Tyr Leu Thr Glu Ala
65                 70                 75                 80

Lys Val Glu Lys Leu Cys Val Trp Asn Asn Lys Thr Pro His Ala Ile
                85                 90                 95

Ala Ala Ile Ser Met Ala Asn
            100
```

<210> SEQ ID NO 18

-continued

```
<211> LENGTH: 103
<212> TYPE: PRT
<213> ORGANISM: Vibrio cholerae

<400> SEQUENCE: 18

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
                20                  25                  30

Gly Lys Arg Glu Met Ala Ile Ile Thr Phe Lys Asn Gly Ala Thr Phe
            35                  40                  45

Gln Val Glu Val Pro Gly Ser Ala His Ile Asp Ser Gln Lys Lys Ala
        50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 19
<211> LENGTH: 103
<212> TYPE: PRT
<213> ORGANISM: Escherichia coli

<400> SEQUENCE: 19

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
                20                  25                  30

Gly Lys Arg Glu Met Val Ile Ile Thr Phe Lys Ser Gly Glu Thr Phe
            35                  40                  45

Gln Val Glu Val Pro Gly Ser Gln Ser Ile Asp Ser Gln Lys Lys Ala
        50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Ile Ser Ile
                85                  90                  95

Ala Ala Ile Ser Met Glu Asn
            100
```

MUTANT FORMS OF ETXB AND CTXB AND THEIR USE AS CARRIERS

CROSS-REFERENCE TO RELATED APPLICATIONS

Figure 1:
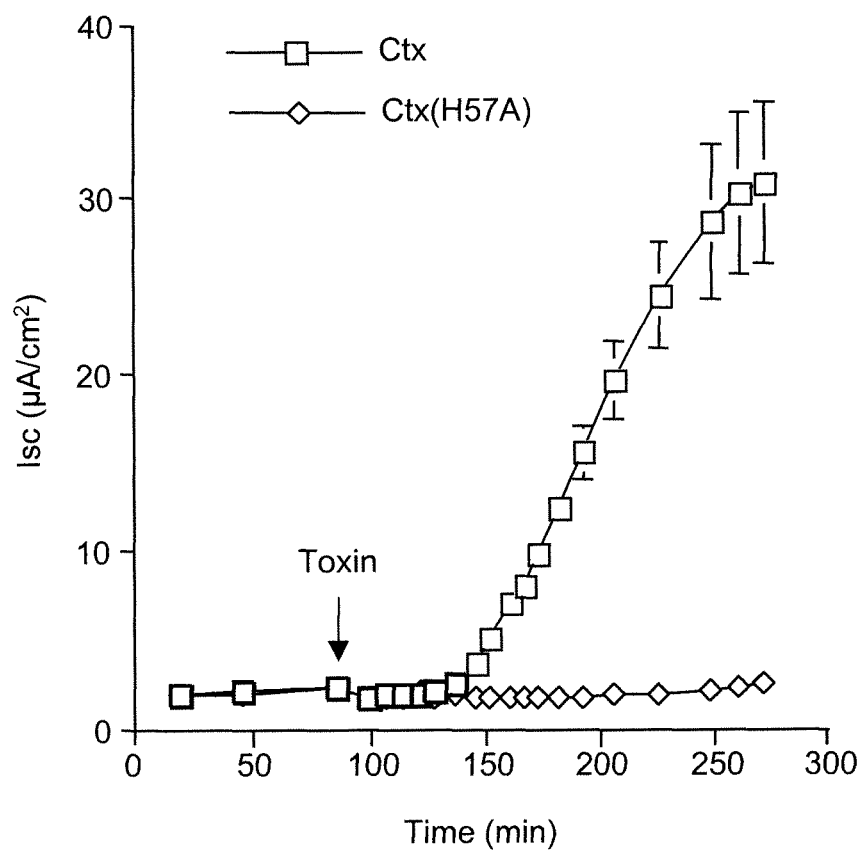

This application is a continuation of pending U.S. patent application Ser. No. 10/743,391 filed 22 Dec. 2003, which is a continuation of International Patent Application No. PCT/GB2002/002829 filed 20 Jun. 2002, which designated the United States and claims priority of British Application No. 0115382.4 filed 22 Jun. 2001.

FIELD OF THE INVENTION

The present invention relates to improved delivery/targeting vehicles.

More in particular, the present invention relates to the use of mutant forms of EtxB, or CtxB as vehicles to deliver and/or target an agent to a target site.

In particular, the present invention relates to the use of mutant forms of EtxB or CtxB as vehicles to deliver an agent to a target site for the treatment of a disease or condition in a subject in need of the same.

BACKGROUND OF THE INVENTION

EtxB and CtxB as Carrier Molecules for the A Subunit

*Escherichia coli* (*E. coli*) heat labile enterotoxin (Etx) and its closely related homologue, cholera toxin (Ctx) from *Vibrio cholerae*, are examples of protein toxins which bind to glycolipid receptors on host cell surfaces. Each toxin consists of six noncovalently linked polypeptide chains, including a single A subunit (27 kDa) and five identical B subunits (11.6 kDa) which bind to GM-1 ganglioside receptors found on the surfaces of mammalian cells (Nashar et al 1996 Proc Natl Acad Sci 93: 226-230). The A subunit is responsible for toxicity possessing adenosine diphosphate (ADP) ADP-ribosyltransferase activity, whereas the B subunits (EtxB and CtxB) are non-toxic oligomers which bind and cross-link a ubiquitous cell surface glycolipid ganglioside, called GM-1, thus facilitating A subunit entry into the cell.

B Subunit is a Potent Immunogen

In contrast to the poor immunogenicity of the A subunit alone, both EtxB and CtxB are exceptionally potent immunogens and their respective holotoxins, Etx and Ctx (which comprise the A and B subunits) are known to be potent adjuvants when given orally in combination with unrelated antigens (Ruedl et al 1996 Vaccine 14: 792-798; Nashar et al 1993 Vaccine 11: 235; Nashar and Hirst 1995 Vaccine 13: 803; Elson and Ealding 1984 J Immunol 133: 2892; Lycke and Holmgren 1986 Immunology 59: 301). Because of their immunogenicity, both EtxB and CtxB have been used as carriers for other epitopes and antigens (Nashar et al 1993 ibid) and have been used as components of vaccines against cholera and *E. coli* mediated diarrhoeal diseases (Jetborn et al 1992 Vaccine 10: 130).

B Subunit is a Potent Immunomodulator

We have demonstrated the surprising finding that the EtxB subunit is also capable of acting as an immunomodulator in immune disorders. In this respect, we have disclosed in WO 97/02045 that EtxB binds to GM-1 ganglioside receptors which are found on the surfaces of mammalian cells and that this binding induces differential effects on lymphocyte populations including a specific depletion of CD8+ T cells and an associated activation of B cells.

One of the most unexpected and sting effects of the B-subunits is their capacity to trigger the selective apoptosis of CD8+ T-cells, as well as to alter CD4+ T-cell differentiation, activate B-cells and modulate antigen processing and presentation by macrophages (Williams, N. A., Hirst, T. R. & Nashar, T. O. (1999) Immunol. Today 20, 95-101.). These potent immunological properties have led to testing of the B-subunits as adjuvants for stimulating mucosal and systemic responses to co-administered antigens (Verweij, W. R., de Haan, L., Holtrop, M., Agsteribbe, E., Brands, R., van Scharrenburg, G. J. M. & Wilschut, J. (1998) Vaccine 16, 2069-2076. Richards, C. M., Aman, A. T., T. R., Hill, T. J. & Williams, N. A. (2001) Journal of Virology 75, 1664-1671.); and as agents for down-regulating proinflammatory autoimmune diseases such as rheumatoid arthritis and diabetes (Williams, N. A., Stasiuk, L. M., Nashar, T. O., Richards, C. M., Lang, A. K., Day, M. J. & Hirst, T. R. (1997) Proc. Natl. Acad. Sci. (USA) 94, 5290-5295).

Mutant B Sub-Units—No Gm-1 Binding—No Immunomodulation

These effects are absent when a mutant EtxB protein (G33D) (lacking GM-1 binding activity) is employed. Consequently, these experimental results suggested that all of the functionalities associated with EtxB and CtxB are attributable to the capacity of the EtxB and CtxB subunits to bind to the GM-1 receptor and that immunomodulation and other effects of Etx and Ctx are mediated through GM-1 binding since mutants lacking the capacity to bind GM-1 (such as EtxB (G33D)) fail to act as adjuvants or immunomodulators.

It is well known that CtxB and EtxB contain an extensive conserved segment spanning residues 45 to 74 that contains an exposed loop from Val-52 (V52) to Ile-58 (I58) located on the lower convoluted surface of the molecule (Hirst, T. R. (1999) in The Comprehensive Sourcebook of Bacterial Protein Toxins, ed. Freer, J. E. A. a. J. H. (Academic Press, London), pp. 104-129). This loop is normally oriented towards the cell membrane and forms part of the GM1-binding surface, with residues Gln-56, His-57 and Ile-58 involved in a network of solvent-mediated hydrogen bonds that is conserved in the presence of bound GM1-pentasaccharide (Merritt, E. A., Sixma, T. K., Kalk, K. H., Van Zanten, B. A. M. & Hol, W. G. J. (1994) Mol. Microbiol. 13, 745-753.).

Mutant B Sub-Units—Gm-1 Binding—No Immunomodulation

We have demonstrated in WO 00/14114 that CtxB molecules with point mutations at three separate sites within the β4-α2 loop (positions 51, 56 and 57) retained GM-1 binding activity, but lacked other activities, such as toxicity and the capacity to upregulate CD25 and trigger apoptosis of CD8-positive T-cells. We have also shown that EtxB molecules with point mutations in position H57 of EtxB showed a similar loss in triggering/modulation of immune cell populations. In addition, Ctx holotoxins comprising B subunits with mutations also showed a defect in an ability to trigger electrogenic chloride secretion, the primary secretory event responsible for mediating diarrhorea. These findings clearly demonstrated that CtxB and EtxB molecules with point mutations within the β4-α2 loop were capable of binding to the GM-1 receptor but were lacking in an immunomodulatory effect which suggested that not all of the effects of Etx and Ctx and in particular, the immunomodulatory effects, were mediated through but not exclusively by GM-1 binding.

In particular, WO 00/14114 confirmed the importance of the B-subunit E51-I58 loop, and in particular H57 in mediating the immunomodulatory properties of the molecule. The teachings in WO 00/14114 demonstrated that the β4-α2 loop of EtxB/CtxB is responsible for a secondary binding activity and so the use of this loop in isolation from the rest of the EtxB/CtxB molecule (for example as a peptide), may permit the secondary binding activity to occur in the absence of the first. Thus, the selective mutation of the β4-α2 loop, or a peptide derived from this loop, may be exploited with a view to increasing the affinity of the secondary binding activity. By increasing the affinity of the secondary binding activity, the interaction with GM-1 may be further obviated. In summary, the teachings in WO 00/14114 demonstrated that the "secondary" binding activity of an isolated "loop" peptide is not necessarily dependent on a primary GM-1 binding event as is found with full length CtxB and EtxB to mediate the immunomodulatory response.

Thus, it is clear from the above studies that the wild type B subunit is a potent immunogen and a potent immunomodulator whereas the mutations in the B subunit can result in either no GM-1 binding and no immunomodulation or the retention of GM-1 binding but with no immunomodulatory capability.

The Immunological Mechanisms Underlying the Use of the B-Subunit.

The B-subunits ability to modulate the immune response is dependent on its capacity to modulate the activity of T-cells, B-cells and populations of antigen presenting cells. Each of these cell types plays a critical role in the development of the immune response. In the normal response to a foreign organism, antigens are internalised by antigen presenting cells, of which professional antigen presenting cells, such as dendritic cells are the most important. These cells are specialised in breaking down proteins into short amino acid sequences (peptides) which associate with major histocompatibility complex (MHC) molecules which are then transported to the cell surface. Foreign peptides bound to class II MHC molecules are recognised by T-helper cells (CD4+ T-cells) which are activated as a result and begin to divide, differentiate and secrete hormone-like messengers called cytokines. The T-helper cells then co-ordinate and maintain the immune response.

Subsequent responses can involve the activation of i) B-cells which mature into plasma cells capable of producing antibodies, ii) macrophages and neutrophils which enter the sites of infection and ingest foreign material leading to its destruction, and iii) other types of T-cell (CD8+ T-cells) which can recognise virally infected cells of the body and kill them. Most normal immune responses will involve activation of all of these components to some extent. However, it is clear that certain factors can affect which particular components are dominant.

In addition, in certain circumstances it is clearly beneficial to be able to tailor which type of response is elicited. By way of example, it is well known that cytotoxic T lymphocytes (CTLs) play a central role in immune surveillance by recognising foreign antigenic peptides bound to MHC class I molecules and killing virally infected and potentially cancerous cells. Thus, it would be beneficial to tailor the immune response in the direction of the cytotoxic T-cell responses in order to facilitate the removal of infectious agents which reside within cells of the body, such as viruses and certain bacteria.

The effective induction of cytotoxic T-cell responses requires the entry of antigens into the cytosol of antigen presenting cells where they can enter the endogenous class I processing and presentation pathway. However, current immunisation strategies, using peptide or protein antigens, generally fail to elicit a CTL response since these antigens are unable to or are able to only partially access the intracellular compartments where loading of class I molecules occurs.

Thus, an efficient delivery system which results in the targeting of antigens into the cytosol is required.

It is known that either wild type EtxB or CtxB may be used as vehicles for the delivery of attached peptides into cells such as MHC Class I bearing cells or professional APCs to achieve the presentation of the such antigenic determinants by MHC class I molecules. The teachings in WO 99/58145 also indicate that the wild type EtxB or CtxB free from of whole toxin, may be used in a conjugate with a peptide or an antigenic determinant to target their delivery to a cell.

One potential disadvantage associated with the use of wild type EtxB or Ctx B is that the potent immune responses engendered to these molecules may preclude their repeated use as drug vehicles. Another potential disadvantage with the use of wild type EtxB or CtxB is that their immunomodulatory capabilities downregulate or suppress certain T-helper responses, that in other circumstances may be beneficial in engendering a preferred or beneficial immune response. Thus, it is desirable to find new ways for delivering an agent to an intracellular compartment of a target cell without triggering a potent immunomodulatory response or a potent immune response such as that induced by wild type CtxB or EtxB molecules.

SUMMARY OF THE INVENTION

The present invention now provides the use of a mutant form of EtxB or CtxB to deliver an agent to a target cell wherein the mutant has GM-1 binding activity; but wherein the mutant has a reduced immunogenic and immunomodulatory activity relative to the wild type form of EtxB or CtxB.

Other aspects of the present invention are presented in the accompanying claims and in the following description and discussion. These aspects are presented under separate section headings. However, it is to be understood that the teachings under each section heading are not necessarily limited to that particular section heading.

Surprising/Unexpected Findings

We have now found mutant forms of CtxB and EtxB which bind GM-1 receptors that are capable of acting as delivery vehicles but which do not trigger either a potent immunomodulatory or a potent anti-carrier immune response (that is, a potent immunogenic response). The mutant forms/derivatives of CtxB and EtxB of the present invention can bind GM-1 and enter mammalian cells, even though they have a reduced immunogenicity and a reduced immunomodulation capability.

Although workers in the field knew that the GM-1 receptor acts as a functional receptor for Ctx/CtxB and Etx/EtxB, there was no disclosure or suggestion in the prior art of the possibility that mutant forms of CtxB or EtxB which bind to GM-1 but which do not have any potent immunogenic or immunomodulatory effect—could be used as vehicles for delivering agents into mammalian cells without inducing any possible undesirable side effects which could preclude repeated use of the carrier moiety.

The present invention is advantageous because the ability of the mutant forms of CtxB and EtxB to enter mammalian cells without inducing a potent anti-B-subunit response and immunomodulatory response means that the mutants are better drug or peptide delivery vehicles for agents, such as drugs or antigenic peptides, than the corresponding wild-type EtxB or CtxB molecules.

The present invention is also advantageous because the mutant of the present invention, which has an effect on vesicular internalisation mediated by GM1-binding may be linked, by for example, conjugation with an agent, such as an antigen or an antigenic determinant, to upregulate the presentation of the antigen or the antigenic determinant, or the antigenic determinant derived from said antigen, by MHC class I molecules to stimulate CTL responses.

The delivery of agents, such as antigens or antigenic determinants, is advantageous because the delivery allows the presentation of agents, such as antigens or antigenic determinants on MHC class I molecules, which can lead to the induction of class I restricted T-cell responses. As indicated above, such responses are beneficial in affording protection against diseases and conditions such as viral infections and cancers.

The delivery of agents, such as pro-drugs, using the mutant forms of CtxB and EtxB is especially advantageous if the prodrug is activated by entry into acidic endosomes. In addition, the present invention is advantageous because the mutant forms of CtxB or EtxB may be manipulated to selectively deliver one or more agents to the cytosol and/or the nucleus of a mammalian target cell.

Other advantages are discussed and are made apparent by the following commentary. Ctx/CtxB As used herein, the term "Ctx" refers to the cholera toxin and "CtxB" to the B subunit of the cholera toxin (SEQ. ID NO: 12). In other texts, these may sometimes be identified as "CT" or "Ct" and "CTB" or "CtB" respectively.

Etx/EtxB

The term "Etx" herein means the $E.$ $coli$ heat labile enterotoxin, and "EtxB" is the B subunit of Etx (SEQ. ID NO: 15). In other texts, these may sometimes be identified as "LT" or "Lt" and "LTB" or "LtB" respectively.

Wild Type CtxB and EtxB

As used herein the term "wild type CtxB or EtxB" refers to a CtxB or EtxB molecule with an activity which is substantially the same as the native CtxB or EtxB molecules. That is, the term includes molecules which retain the capacity to bind GM1 and/or the capacity to mimic the effects of binding to GM1 and which retain the immunomodulatory capability of these B subunits.

Mutant Forms of CtxB and EtxB

As used herein, the term "mutant form of CtxB and EtxB" refers to a CtxB or EtxB subunits and variants or derivatives thereof as well as variants and/or derivatives of the nucleotide sequence coding for these protein molecules which retain the capacity to bind GM1 and/or the capacity to mimic the effects of binding to GM1 but which do not retain the potent immunogenic and immunomodulatory properties observed with the wild type EtxB or CtxB subunits or which have substantially reduced immunogenic and immunomodulatory activity relative to the wild type EtxB or CtxB subunits. A mutant form of CtxB or EtxB may arise naturally, or may be created artificially (for example by site-directed mutagenesis or by additions, substitutions or deletions in the sequences comprising or encoding the mutant forms of CtxB or EtxB. By way of example, a mutant form of CtxB or EtxB may result from mutation in the β4-α2 loop of CtxB or EtxB.

Preferably the mutation is in the region spanning amino acid residues E51-I58 of the β4-α2 loop of CtxB or EtxB (SEQ. ID NO: 1).

Preferably the mutation is at amino acid residues 51 (SEQ. ID NO: 17), 56 (SEQ. ID NO: 18) and/or 57 (SEQ. ID NOS: 13, 16 and 19) of the β4-α2 loop of CtxB or EtxB (SEQ. ID NO: 2).

Preferably the mutation is a point mutation in the His57 amino acid (SEQ. ID NO: 3). Preferably the mutation is an alanine (A) or a serine (S) amino acid (hereinafter referred to as either a H57A (SEQ. ID NO: 13) or H57S (SEQ. ID NO: 19) mutation).

The terms "variant" or "derivative" in relation to the mutant EtxB or CtxB subunits of the present invention includes any substitution of, variation of, modification of, replacement of, deletion of or addition of one (or more) amino acids from or to the amino acid sequence comprising the wild type EtxB or CtxB molecule or any substitution of, variation or modification of the nucleotide sequence encoding the wild type EtxB or CtxB subunits providing the resultant entity retains a GM-1 binding activity but does not retain the same and/or similar potent immunogenic and immunomodulatory properties as the wild type CtxB or Etx subunits or which has substantially reduced immunogenic and immunomodulatory activity relative to the wild type EtxB or CtxB subunits. The variant or derivative need not be derived from the wild type EtxB or CtxB. By way of example, the variant or derivative may be expressed and/or synthesised from or by using suitable starting products so that the final product mimics the activity of the mutant form of CtxB and/or EtxB.

The term "mutant form of CtxB and EtxB" may be referred to interchangeably as the "mutant form" of the B subunit throughout the text or just the "mutant" of the present invention.

For the avoidance of doubt, the term "mutant form of CtxB and EtxB" does not include the wild type form of CtxB and EtxB.

Preparation of Mutant Forms of CtxB and EtxB.

The mutant forms of CtxB and EtxB as used herein include natural forms of the molecule which have been isolated and recombinant and/or synthetic forms of the molecules.

Preferably the mutant forms of CtxB and EtxB are prepared using recombinant means.

The recombinant mutant forms of CtxB and EtxB may be produced by a method in which the gene or genes coding for the specific polypeptide chain (or chains) from which the mutant B subunit is formed, is inserted into a suitable vector and then used to transfect a suitable host. For example, the gene coding for the polypeptide chain of the EtxB subunit may be inserted into, for example, a plasmid vector pMMB66EH to generate pMMB68 which is then used to transfect host cells, such as $Vibrio$ sp. 60. The protein is purified and isolated in a manner known per se. Mutant genes expressing active mutant CtxB and EtxB subunits may be produced by known methods from the wild type genes CtxB and EtxB subunits.

Preferably, the mutant forms of CtxB and EtxB are substantially isolated and/or substantially pure and/or substantially free of toxin.

As used herein, the terms "isolated" and "purified" refer to molecules, either nucleic or amino acid sequences, that are removed from their natural environment and/or isolated or separated from at least one other component with which they are naturally associated. A protein may be mixed with carriers or diluents which will not interfere with the intended purpose of the substance and still be regarded as substantially isolated.

GM-1 Ganglioside Receptor (GM-1 or GM1)

The GM1 ganglioside receptor is a member of family of gangliosides comprising sialic acid containing glycolipids (also called glycosphingolipids) which are formed by a hydrophobic portion, the ceramide, and a hydrophilic part, that is the oligosaccharide chain. Gangliosides are defined as any ceramide oligosaccharide carrying, in addition to other sugar residues, one or more sialic residues (Oxford Dictionary of biochemistry and molecular biology. Oxford University Press. 1997. Eds Smith A D, Datta S P, Howard Smith G, Campbell P N, Bentley R and McKenzie H A). Although first described in neural tissue, several studies have shown that gangliosides are almost ubiquitous molecules expressed in all vertebrate tissues. Within cells, gangliosides are usually associated with plasma membranes, where they may act as receptors for a variety of molecules and take part in cell-to-cell interaction and in signal transduction. In addition, gangliosides are expressed in cytosol membranes like those of secretory granules of some endocrine cells such as the pancreatic islets and adrenal medulla.

Gangliosides contain in their oligosaccharide head groups one or more residues of a sialic acid which gives the polar head of the gangliosides a net negative charge at pH 7.0. The sialic acid usually found in human gangliosides is N-acetyl-neuraminic acid. Over 20 different types of gangliosides have been identified, differing in the number and relative positions of the hexose and sialic residues which form the basis of their classification. Nearly all of the known gangliosides have a glucose residue in glycosidic linkage with ceramide, residues of D-galactose and N-acetyl-D-galactosamine are also present.

In the ganglioside nomenclature of gangliosides, devised by Svennerholm (Biochemistry Lehninger 2nd Ed 1975 Worth Publishers Inc p 294-295) the subscript letters indicate the number of sialic groups. M is monosialo, D is disialo and T is trisialo.

One of the best studied members of the ganglioside family is the monosialylganglioside, GM1, which has been shown to be the natural receptor for the cholera toxin. Soluble ganglioside GM1 binds to the toxin with high affinity and inactivates it (Svennerholm 1976 Adv Exp Med Biol 71: 191-204).

The chemical formula for GM1 can be represented as:

Gal $\beta$3GalNac $\beta$4(NeuAc $\alpha$3)Gal $\beta$4Glc $\beta$1 Cer where Glc is D-glucose, Gal is D-galactose, GalNAc is N-acetyl-D-galactosamine; NeuAc is N-acetylneuraminic acid, Cer is ceramide.

The chemical formula for GM1 can also be represented as galactosyl-N-acetylgalactosaminyl {sialosyl}lactosyl ceramide or galactosyl-N-acetyl-galactosaminyl-(sialyl)-galactosylglusosylceramide.

The x-ray crystal structures of Etx bound to lactose (Sixma et al 1992 Nature (London) 355: 561-564) and CtxB bound to the pentasaccharide of GM 1 (Merritt et al 1994 Protein Sci 3: 166-175) have revealed that CtxB and EtxB bind to the terminal galactose and sialic acid moieties of GM1 and that such binding does not induce any striking changes in B subunit conformation.

GM-1 Binding Activity

The term "GM1 binding activity" refers to an entity such as a CtxB or EtxB subunit or a mutant form thereof which is capable of interacting with a GM1 ganglioside receptor.

An assay for determining GM-1 binding activity would be readily determinable to those skilled in the art. For example, the assay may utilise GM-1 bound to a solid support and wherein the substance is then passed across the bound GM-1. Non-elution of the mutant form is indicative that it does bind to GM-1. In a more preferred aspect, the assay is that described in WO 97/02045.

Immunogenic

As used herein, the term "immunogenic" means an anti-B subunit response (also referred to as an anti-carrier response). The term "immunogenic" does not mean a response against any antigen associated with the B subunit and/or any antigen which the B subunit might carry.

Immunomodulator

The term "immunomodulator" or "immunomodulatory molecule" or "immunomodulatory factor(s)" refer to molecules or factors that, when made by one or more cells involved in an immune or inflammatory response, or which when added exogenously to the cells, causes the immune or inflammatory response to be different in quality or potency from that which would have occurred in the absence of the factor.

An immunomodulator may modulate the immune response by altering, for example, the specific reactivity or the nonspecific effector associated mechanisms of the host. By way of example, an immunomodulator may trigger cell-signalling events or induce potent anti-B-subunit immune responses or be capable of inducing, for example, a differential effect on cells, such as lymphocyte cells—preferably leading to induction of apoptosis in CD8+ T cells and/or enhanced activation of CD4+ cells and/or the polyclonal activation of B cells and/or a modulation in the expression and/or levels of immunostimulatory molecules such as cytokines, lymphokines and/or immune co-factors. The term "differential effect on leukocyte cells" may include but is not limited to a specific depletion of CD8+ cells (through for example apoptosis), the enhanced activation of CD4+ T cells (T helper cells (Th)) and/or an associated activation of B cells. The immunomodulator may also be capable of down-regulating the pathological response of Th1 and/or Th2-associated immune responses and upregulating the production of antibodies at mucosal surfaces.

Immunomodulation

The immunomodulatory effects observed with wild type EtxB or CtxB may be GM-1 mediated intracellular signalling effect which may be triggered by GM-1 binding. Without being bound by theory, the binding of the B-subunits to receptors such as GM1 triggers signal transduction and induce toxin internalisation. The pentameric cross-linking of the GM1 receptor causes local alterations in membrane dynamics and the microlipid environment, which in turn influences the activity of integral membrane proteins that participate in cell-signalling or alternatively may permit direct or indirect interaction of bound CtxB or EtxB molecules with membrane associated molecules responsible for triggering signalling that result in immunomodulation.

Immunomodulation Assay

An assay for determining whether a mutant form of EtxB or CtxB has immunomodulatory properties would be readily determinable to those skilled in the art. For example, the assay may measure and/or determine an effect on cell populations, such as lymphocyte cell populations. These effects can include but are not limited to an induction of apoptosis in CD8+ T cells, the enhanced activation of CD4+ T cells (Th cells) and the polyclonal activation of B cells. In addition, or in the alternative, the assay could be based on determining and/or measuring particular cell surface marker(s) indicative of activation of certain intracellular events (e.g. measuring an increase in CD25 expression). The quality or potency of a response may be measured by a variety of other assays known to one skilled in the art. These assays may include but are not limited to in vivo studies such as whole animal studies for immunogenic and/or immunomodulatory responses or in vitro studies for measuring same.

Agent

The mutant forms of CtxB or EtxB of the present invention may be used to deliver an agent to a target mammalian cell. As used herein, the term "agent" can include but is not limited to a peptide of interest or a protein sequence of interest (POI), an antigen, an antigenic determinant, an antibody and a nucleotide sequence of interest (NOI). The term "agent" can include one or more agents. By way of example, the mutant of the present invention may be used to delivery one or more POI(s), one or more antigen(s) and/or one or more antigenic determinant(s) and/or one more NOI(s) to a target mammalian cell. The agent can be a therapeutic and/or a diagnostic agent.

Membrane-Translocating or Fusigenic Peptide

The term membrane-translocating or fusigenic peptide is used herein to refer to any peptide that interacts with and/or penetrates a mammalian cell membrane. By way of example, a membrane translocating or fusigenic peptide may comprise a viral protein and may comprise elements of the Pol-loop segment, corresponding to a domain in the C-terminal region of HSV-1 polymerase.

Antigen

Preferably the antigen is derivable from a tumour associated antigen (TAA).

TAA

The term "tumour associated antigen (TAA)" is used herein to refer to any TAA or antigenic peptide thereof. The antigen being one that is expressed by the tumour itself or cells associated with the tumour such as parenchymal cells or those of the associated vasculature. The term "tumour associated antigen (TAA)" includes antigens that distinguish the tumour cells from their normal cellular counterparts where they may be present in trace amounts.

Alternatively, the antigen also be derived from pathogenic agents derived from tumour cells which multiply unrestrictedly in an organism and may thus lead to pathological growths. Examples of such pathogenic agents are described in Davis, B. D. et al (Microbiology, 3rd ed., Harper International Edition). These antigens may include tumour associated antigens (TAA) which can serve as targets for the host immune system and elicit responses which result in tumour destruction. Examples of such antigens include but are not limited to MART-1 (Melanoma Antigen Recognised by T cells-1) MAGE-1, MAGE-3, 5T4, gp100, Carcinoembryonic antigen (CEA), prostate-specific antigen (PSA), MUCIN (MUC-1), tyrosinase.

Infectious Agent

Preferably the antigen is derivable from an infectious agent.

Preferably the antigen is derivable from a viral antigen.

In one embodiment of the present invention, the antigen may be derived from pathogenic viruses. These include but are not limited to Human Immunodeficiency Virus (HIV) (GP-120, p17, GP-160 antigens), influenza (NP, HA antigen), herpes simplex (HSVdD antigen), human papilloma virus, equine encephalitis virus, hepatitis (Hep B Surface Antigen), feline leukaemia virus, canine distemper, rabies virus, epstein barr virus (EBV), influenza virus.

In another embodiment of the present invention, the antigenic determinant may be derived from pathogenic bacteria which include but are not limited to *Chlamydia, Mycobacteria, Plasmodium Falciparum*, and *Legionella*. Pathogenic protozoans include but are not limited to malaria, *Babesia, Schistosoma, Toxiplasma* and *Toxocara canis*. Pathogenic yeast include *Aspergillus* and invasive *Candida* In a preferred embodiment the pathogenic microorganism is an intracellular organism.

If the infectious agent is selected from the group consisting of enteropathogenic, enterotoxigenic, enteroinvasive, enterohaemorrhagic and enteroaggregative *E. coli*, then the antigenic determinant may be an antigenic determinant of a bacterial toxin or adhesion factor.

Isolation of an Antigen of Interest

There are a number of known methods by which it is possible to isolate an antigen of interest. For example, an antigenic agent comprising one or more potential protective antigens may be extracted from the agent, or from cells infected by the agent, by use of procedures that allow the recovery of the antigens. This may include the use of cell disruption techniques to lyse cells such as sonication and/or detergent extraction. Centrifugation, ultrafiltration or precipitation may be used on collected antigen preparations. The antigen preparation containing HSV-1 glycoproteins described in Richards et al., (1998) J. Infect. Dis. 177; 1451-7, exemplifies such a method.

Also, antigens of an antigenic agent, or from cells infected by a said agent may be extracted by a variety of procedures, including but not limited to, urea extraction, alkali or acid extraction, or detergent extraction and then subjected to chromatographic separation. Material recovered in void or elution peaks comprising one or more potential protective antigens may used in vaccine formulations.

Alternatively, genes encoding one or more potential protective antigens may be cloned into a variety of expression vectors suitable for antigen production. These may include bacterial or eukaryotic expression systems, for example *Escherichia coli, Bacillus* spp., *Vibrio* spp. *Saccharomyces cerevisiae*, mammalian and insect cell lines. Antigens may be recovered by conventional extraction, separation and/or chromatographic procedures.

Antigenic Determinant

Preferably the agent is an antigenic determinant. The term "antigenic determinant" as used herein refers to a site on an antigen which is recognised by a T-cell receptor or an antibody. Preferably it is a short peptide derived from or as part of a protein antigen. However the term is also intended to include peptides with glycopeptides and carbohydrate epitopes. The term also includes modified sequences of amino acids or carbohydrates which stimulate responses which recognise the whole organism.

It is advantageous if the antigenic determinant is an antigenic determinant of an infectious agent (such as a bacterium or virus) which causes the infectious disease.

Viral Antigenic Determinant

The antigenic determinant may be derived from pathogenic viruses. These include but are not limited to Human Immunodeficiency Virus (HIV) (GP-120, p17, GP-160 antigens), influenza (NP, HA antigen), herpes simplex (HSVdD antigen), human papilloma virus, equine encephalitis virus, hepatitis (Hep B Surface Antigen), feline leukaemia virus, canine distemper, rabies virus, epstein barr virus (EBV), influenza virus.

By way of example, if the infectious agent is EBV, the antigenic determinant may be an antigenic determinant of gp340 or gp350 or of a latent protein, such as, for example, EBNAs 1, 2 3A, 3B, 3C and -LP, LMP-1, -2A and 2B or an EBER.

If the infectious agent is an influenza virus, the antigenic determinant may be derivable from an internal protein (for example, nucleoprotein) or the antigenic determinant may be derivable from a viral coat protein, such as, for example, haemagglutinin and neuraminidase.

Preferably the antigenic determinant of an immediate early, early or late gene product of a virus, such as the herpes virus.

Preferably the antigenic determinant is derivable from an internal protein (for example, nucleoprotein) or a viral coat protein, such as, for example, haemagglutinin and neuraminidase.

Bacterial Antigenic Determinant

If the infectious agent is selected from the group consisting of enteropathogenic, enterotoxigenic, enteroinvasive, enterohaemorrhagic and enteroaggregative *E. coli*, then the antigenic determinant may be an antigenic determinant of a bacterial toxin or adhesion factor.

The antigenic determinant may also be derived from pathogenic bacteria which include but are not limited to *Chlamydia, Mycobacteria, Plasmodium Falciparum*, and *Legionella*. Pathogenic protozoans include but are not limited to malaria, *Babesia, Schistosoma, Toxiplasma* and *Toxocara canis*.

Tumour Associated Antigenic Determinants

Alternatively, the antigenic determinant may also be derived from pathogenic agents derived from tumour cells which multiply unrestrictedly in an organism and may thus lead to pathological growths. Examples of such pathogenic agents are described in Davis, B. D. et al (Microbiology, 3rd ed., Harper International Edition). These antigenic determinant may include tumour associated antigens (TAA) which can serve as targets for the host immune system and elicit responses which result in tumour destruction. Examples of such antigens include but are not limited to MART-1 (Melanoma Antigen Recognised by T cells-1) MAGE-1, MAGE-3, 5T4, gp100, Carcinoembryonic antigen (CEA), prostate-specific antigen (PSA), MUCIN (MUC-1), tyrosinase.

There are a number of known methods by which it is possible to identify antigenic determinants for a given antigenic agent. For example, potential protective antigens may be identified by elevating immune responses in infected or convalescent patients, in infected or convalescent animals, or by monitoring in vitro immune responses to antigen containing preparations.

Other TAAs may be identified, isolated and cloned by methods known in the art such as those disclosed in U.S. Pat. No. 4,514,506.

Delivery of Mutant and Agent

The mutant and agent of the present invention may be linked to form a single entity.

Linked

As used herein, the term "linked" which is synonymous with the term "coupled" means the mutant and agent may be linked by a variety of methods to facilitate the translocation of the agent to the target cell, preferably into the cytosol and/or the nucleus of a mammalian target cell.

The term "linked" or "linkage" includes but is not limited to genetic linkage and chemical conjugation. The linkage of the mutant with the agent also includes but is not limited to direct linkage (such as by an ionic or a covalent bond) or indirect linkage, for example, by the provision of suitable spacer groups. By way of example, the agent and the mutant may be covalently linked, to form a single active moiety/entity. The mutant and/or agent may also be linked to another entity.

Chemical Linkage

In one embodiment of the present invention, the mutant of the present invention is chemically conjugated to the agent. Preferably the mutant is conjugated to the agent using a bifunctional cross-linking reagent, such as a heterobifunctional cross-linking reagent. More preferably the cross-linking agent is N-.gamma.(-maleimido-butyroxyl)-succinimide ester (GMBS) or N-succinimidyl-(3-pyridyl-dithio)-propionate (SPDP).

Even more preferably, the agent is conjugated to EtxB by the use of the chemical bifunctional, cross-linker, N-(gamma-maleimido-butyryl-oxy), succinimide (GMBS) (Pierce).

Genetic Linkage

In another embodiment of the present invention, the mutant and agent are genetically linked either directly to form a fusion protein or indirectly, by for example, spacers or insulators. Preferably the agent such as an antigen or antigenic determinant, is genetically linked to amino or the C-terminus of the mutant form of the B subunit.

Preferably, the fusion protein comprises an antigen or an antigenic determinant which is fused to the mutant of the present invention. The antigen or antigenic determinant may be attached to either the amino or carboxy terminus of the mutant.

Linkage to Enhance CTL Activation

In one preferred embodiment of the present invention, the mutant of the present invention, which targets vesicular internalisation mediated by GM1-binding may be linked, by for example, conjugation with an agent, such as an antigen or an antigenic determinant, to upregulate the presentation of the antigen or the antigenic determinant, or the antigenic determinant derived from said antigen, by MHC class I molecules to stimulate appropriate CTL responses. The stimulation of CTL responses is particularly useful in the prevention and treatment of viral infections, such as, for example influenza and in stimulating responses to a tumour associated antigen (TAA).

Cytotoxic T Lymphocytes (CTLs)

As used herein, the term "Cytotoxic T lymphocytes (CTL)" is used to refer to CTLs which are typically induced or stimulated by the display of a cell surface recognition structure, such as a processed, pathogen-specific peptide, in conjunction with MHC class I on an MHC class I bearing antigen presenting cell (APC). CTLs may function in more than one way. The best known function is the killing or lysis of target cells bearing peptide antigen in the context of an MHC class I molecule. Hence the reason why these cells are termed cytotoxic T lymphocytes (CTL). However, another function, perhaps of greater protective relevance in certain infections is the ability of CTLs to secrete interferon gamma (IFN-.gamma.). Thus, assays of lytic activity and of IFN-.gamma. release are both of value in measuring CTL as an indicator of the cellular immune response.

Antigen Presenting Cell (APC)

As used herein, the term "antigen presenting cell" refers to any cell which is an MHC class I bearing cell. Examples of APCs include but are not limited to hematopoietic stem cells, lymphocytes, vascular endothelial cells, respiratory epithelial cells, keratinocytes, skeletal and cardiac muscle cells, neurons, cancer cells respiratory airway epithelial cells, hepatocytes, muscle cells, cardiac myocytes, synoviocytes, primary mammary epithelial cells and post-mitotically terminally differentiated non-replicating cells such as macrophages or neurons and professional antigen presenting cells (APC) such as dendritic cells or macrophages.

Professional Antigen Presenting Cell (APC)

As used herein, the term "professional antigen presenting cell" refers to a cell, such as a dendritic cell or macrophage, that recognises an antigen to be targeted for neutralisation. The APC takes up the antigen and processes it, incorporating the antigen fragments into its own membrane and presenting them in association with either class I or class II major histocompatability complex (MHC) molecules to T lymphocytes, such as CTLs or T helper cells (Th) which are then stimulated to mount a response.

Target Cells

The mutant of the present invention may be used to deliver one or more agent(s) to a target mammalian cell.

The term "target cell" includes but is not limited to macrophages, endothelial cells or combinations thereof. Further examples include but are not limited to antigen presenting cells (APCs) such as hematopoietic stem cells, lymphocytes, vascular endothelial cells, respiratory epithelial cells, keratinocytes, skeletal and cardiac muscle cells, neurons, cancer cells respiratory airway epithelial cells, hepatocytes, muscle cells, cardiac myocytes, synoviocytes, primary mammary epithelial cells and post-mitotically terminally differentiated non-replicating cells such as macrophages or neurons and professional antigen presenting cells (APC) such as dendritic cells or macrophages.

In a preferred embodiment, the target cell is a vertebrate cell.

In a preferred embodiment, the target cell is a mammalian cell.

In a highly preferred embodiment, the target cell is a human cell.

As used herein, the term "mammal" includes but is not limited to humans, primates, rats, mice, guinea pigs, rabbits, horses, cows, sheep, pigs, goats and the like.

Pharmaceutical Compositions

The present invention also provides a pharmaceutical composition comprising administering a therapeutically effective amount of the substance of the mutant and agent and a pharmaceutically acceptable carrier, diluent or excipients (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration.

The term "administered" includes delivery by non-viral techniques. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Kits

The present invention further provides kits comprising the mutant and the agent. In one embodiment of the present invention, the mutant and agent are presented as a single active moiety. Such kits may be used to treat the diseases and conditions of the present invention.

In one preferred embodiment of the present invention, the agent in the kit may comprise an antigen and/or antigenic determinant and/or a separate adjuvant for coadministration with said composition. Alternatively, the agent in the kit comprises an antibody.

Disorders

The mutant of the present invention may be used to deliver an agent to treat disease such as infectious diseases and or viral infections and/or cancer.

Treatment

It is to be appreciated that all references herein to "treatment" include one or more of curative, palliative and prophylactic treatment. In particular, the term "treatment" includes but is not limited to pre-disease treatment and post-disease treatment. By way of example, a subject in a pre-disease state may be treated to prevent the onset and/or progression of that disease.

Preferably, the term treatment includes at least curative treatment and/or palliative treatment.

The treatment may be for treating conditions associated with a particular disease state.

As with the term "treatment", the term "therapy" includes curative effects, alleviation effects, and prophylactic effects.

The therapy may be on humans or animals.

The therapy may be for treating conditions associated with cancer.

Infectious Diseases

Examples of infectious diseases of the present invention include but are not limited to HSV-1, HSV-2, EBV, VZV, CMV, HHV-6, HHV-7 and HHV-8, hepatitis A, B, C, D and E, *Neisseria meningitides, Haemophilus influenzae* type B and *Streptococcus pneumoniae, Legionella pneumophila* and

*Mycobacterium tuberculosis, Neisseria gonnorheae,* HIV-1, HIV-2 and *Chlamydia trachomatism, E. coli,* rotavirus, *Salmonella enteritidis, Salmonella typhi, Helicobacter pylori, Bacillus cereus, Campylobacter jejuni* and *Vibrio cholerae, Staphylococcus aureus, Streptococcus pyogenes* and *Streptococcus mutans,* malaria, *Trypanasoma* spp., *Taxoplasma gondii, Leishmania donovani* and *Oncocerca* spp.

Cancer Related Diseases

The mutant and agent of the present invention can be introduced into a mammal either prior to any evidence of cancers such as melanoma or to mediate regression of the disease in a mammal afflicted with a cancer such as melanoma. Cancers of mammals which may be treated using the composition of the present invention include but are not limited to melanoma, metastases, adenocarcinoma, thymoma, lymphoma, sarcoma, lung cancer, liver cancer, colon cancer, non-Hodgkins lymphoma, Hodgkins lymphoma, leukemias, uterine cancer, breast cancer, prostate cancer, ovarian cancer, cervical cancer, bladder cancer, kidney cancer, pancreatic cancer and the like.

If the mammal to be treated is already afflicted with cancer or metastatic cancer the mutant and agent can be administered in conjunction with other therapeutic treatments. In this context, the present invention encompasses combination therapy. By combination therapy is meant that the mutant and the agent of the present invention is administered to the patient in combination with other exogenous immunomodulators or immunostimulatory molecules, chemotherapeutic drugs, antibiotics, antifungal drugs, antiviral drugs and the like alone or in combination thereof. Examples of other exogenously added agents include but are not limited to exogenous IL-2, IL-6, interferon, tumour necrosis factor, cyclophosphamide, and cisplatinum, gancyclovir and amphotericin B. In one preferred embodiment, the agent is released from the B subunit after delivery into the cell.

In another preferred embodiment, preferably the linkage of the mutant-agent conjugate may be chosen so that the agent is specifically delivered into the nucleus of a target cell.

In another preferred embodiment, the simultaneous, separate or sequential combination of mutant B subunit may be used to deliver an agent to a target cell and a wild type B subunit may be used to deliver an agent to a target cell.

BRIEF DESCRIPTION OF THE DRAWINGS

The present invention will now be described only by way of example in which reference is made to the following Figures:

FIG. 1 is a graph;

FIG. 2 is a graph;

FIG. 3 is a combined pictorial representation and a graph;

FIG. 4A is a pictorial representation;

FIG. 4B is a graph;

FIG. 4C is a graph;

FIGS. 5A and 5B are pictorial representations;

FIGS. 6A, 6B, 6C are pictorial representations;

FIGS. 6D and 6E are graphs;

FIGS. 7A and 7B are graphs;

FIGS. 8A and 8B are graphs;

FIG. 9 is a series of graphs;

FIG. 10 is a series of pictorial representations;

FIG. 11 is a series of pictorial representations; and

FIG. 12 is a graph.

DETAILED DESCRIPTION OF THE INVENTION

FIG. 1 Ctx (H57A) exhibits a severe defect in toxicity. Time course of electrogenic Cl-secretion induced by the addition of 2 nM Ctx (.quadrature.) or Ctx(H57A) (.diamond-solid.) to the apical surface of T84 cell monolayers (with data points representing the mean.+-.S.E., where n-1-2 independent monolayers). Three independent experiments gave similar results.

FIG. 2 CtxB (H57A) (SEQ. ID NO: 13) retains the ability to bind to GM1 CtxB (.box-solid.) (SEQ. ID NO: 12), CtxB (H57A) (5) (SEQ. ID NO: 13) or EtxB (G33D) (.cndot.) (SEQ. ID NO: 14) at a concentration of 1 μg/ml were serially diluted 3-fold in GM1-coated microtiter plates and the bound B-subunits detected by immunoassay as described in the Methods. Three independent experiments gave similar results.

FIG. 3 CtxB (H57A) (SEQ. ID NO: 13) interaction with CD8+ T-cells. Isolated CD8+ T-cells derived from the MLN were incubated on ice for 1 hour in the absence (PBS control) or presence of 100 nM CtxB (SEQ. ID NO: 12), CtxB(H57A) (SEQ. ID NO: 13) or EtxB(G33D) (SEQ. ID NO: 14), then labelled with either anti-CtxB or anti-EtxB antibodies followed by a goat anti-mouse IgG-FITC secondary conjugate. Cells were analysed by fluorescence microscopy (A) or flow cytometry (B). The flow cytometric trace obtained for PBS treated cells is shown in red and the trace obtained for cells treated with the various B subunits is overlaid in black.

FIG. 4 CtxB (H57A) (SEQ. ID NO: 13) is defective in triggering CD8+ T-cell apoptosis. A. MLN cells were cultured for 48 hours in the absence (PBS control) or presence of 100 nM CtxB (SEQ. ID NO: 12), CtxB(H57A) (SEQ. ID NO: 13) or EtxB(G33D) (SEQ. ID NO: 14), then stained with anti-CD8(PE) and anti-CD4 (FITC) antibodies and analysed by flow cytometry. The percentage of CD8+ T-cells is shown in the lower right hand quadrant. B. MLN cells were cultured in the presence of CtxB (SEQ. ID NO: 12) or CtxB(H57A) (SEQ. ID NO: 13) at concentrations ranging from 10 nM to 2.5 μM, and labelled and analysed as above. The percentage of surviving CD8+ T-cells, compared with PBS treated control cells, was calculated. C. Isolated CD8+ T-cells derived from the MLN were cultured for 18 hours in the absence (PBS control) or with 3.45 μM CtxB (SEQ. ID NO: 12), CtxB (H57A) (SEQ. ID NO: 13) or EtxB(G33D) (SEQ. ID NO: 14), then stained with propidium iodide and analysed by flow cytometry to determine the percentage of cells containing sub-diploid DNA.

FIG. 5 Superimposed crystal structures of wild-type CtxB (SEQ. ID NO: 12) and CtxB(H57A) (SEQ. ID NO: 13). (A). Superposition of the crystal structure of wild-type CtxB (green) (SEQ. ID NO: 12) complexed with GM1-OS (blue) onto the structure of the CtxB(H57A) (SEQ. ID NO: 13) mutant (yellow) complexed with galactose (red). A single receptor-binding site (site H) of the five independent sites is shown. Electron density for the galactose molecule is shown at 2a contours in an ($mF_{obs}$-$F_{calc}$) omit map. The point of maximal difference between the peptide backbones of the wild-type (SEQ. ID NO: 12) and mutant toxins (SEQ. ID. NOS: 13) is at residue Gln 56, where the respective Cα atom positions differ by 7 Å (B). Superposition of the wild-type cholera toxin B (SEQ. ID NO: 12)-pentamer in complex with the receptor oligosaccharide onto the CtxB(H57A) mutant B (SEQ. ID NO: 13)-pentamer. The molecular surface of wild-type CTB (SEQ. ID NO: 12) is shown in green (50-60 loop) and blue. The GM1-oligosaccharide in shown in red. The molecular surface of the H57A mutant (SEQ. ID NO. 13) is shown in yellow (50-60 loop). The terminal galactose residue of the GM1-oligosaccharide is not visible behind the molecular surface of the 50-60 loop which forms one side of its binding site on the protein. At one of the five binding sites the molecular surface of this loop is not shown, so that the underlying protein conformation may be seen.

FIG. 6: Production and characterisation of the EtxB-26mer (SEQ. ID NO: 15-SEQ. ID NO:8) conjugate. Panel A: SDS-PAGE analysis of EtxB-26mer (SEQ. ID NO: 15-SEQ. ID NO:8) conjugate. Lanes: 1, EtxB (SEQ. ID NO: 15) unheated; 2, EtxB (SEQ. ID NO: 15) boiled; 3, EtxB-26mer (SEQ. ID NO: 15-SEQ. ID NO:8), unheated; 4, EtxB-26mer (SEQ. ID NO: 15-SEQ. ID NO:8), boiled. Molecular weight standards in kpa and EtxB (SEQ. ID NO: 15) monomer and pentamer (upper and lower arrows, respectively) are indicated. Panel B and C: Western blot analyses of the same samples probed with mAb 118-8, specific for EtxB (Panel B) (SEQ. ID NO: 15) or a polyclonal antiserum specific for SIINFEKL peptide (SEQ. ID NO: 4) (Panel C). Panel D and E: GM1 binding properties of EtxB-26mer (SEQ. ID NO: 15-SEQ. ID NO:8) conjugate. Serial dilutions of EtxB (SEQ. ID NO: 15) and EtxB-26mer (SEQ. ID NO: 15-SEQ. ID NO:8) were applied to GM1-coated ELISA plates and detected using mAb 118-8 (Panel D) or anti-SIINFEKL (Panel E) as above. Absorbances were plotted against the dilution factor and are given as mean.+−.SD.

FIG. 7: EtxB-mediated delivery of the 26mer peptide (SEQ. ID NO: 8) into the class I presentation pathway. Panel A: Extent of peptide presentation was assessed by analysis of IL-2 release by RF33.70 T-cell hybridoma. JAWSII dendritic cells were incubated with various concentrations of either 8mer (SEQ. ID NO: 4) or 26mer (SEQ. ID NO: 8) peptide alone, EtxB (SEQ. ID NO: 15) and 26mer peptide (SEQ. ID NO: 8) admixed, or EtxB-26mer (SEQ. ID NO: 15-SEQ. ID NO:8) conjugate for 2 h. Concentrations tested were equivalent to the molar concentration of peptide in each sample at 1 pM, 10 pM, 100 pM, 1 nM, 20 nM, 40 nM, 60 nM, 80 nM, and 100 nM, respectively. PBS was used as control. Cells were then fixed with 1% (w/v) paraformaldehyde and incubated overnight with RF33.70 cells. The IL-2 content of harvested medium was determined by ELISA. Duplicate samples were tested and the data are given as mean.+−.SD. Panel B: Detection of MHC-I/SIINFEKL complexes as assessed by FACS analysis using mAb 25D1.16. JAWSII cells were treated with 100 nM 8mer peptide (SEQ. ID NO: 4) (dashed black curve), EtxB-26mer (SEQ. ID NO: 15-SEQ. ID NO:8) conjugate (solid black curve), or PBS (grey filled curve) for 2 h and then sequentially incubated with mAb 25D1.16 and a FITC-labelled secondary antibody followed by flow cytometric analysis.

FIG. 8: EtxB-mediated peptide delivery: Optimisation and kinetics of presentation. Panel A: Effect of truncating or extending the 26-mer peptide (SEQ. ID NO: 8) on the extent and efficiency of EtxB-mediated presentation of the class I epitope. JAWSII cells were incubated for 2 h with the indicated peptides either alone, or admixed with or conjugated to EtxB (SEQ. ID NO: 15) at equivalent peptide concentrations of 100 nM. Cells were then fixed with 1% (w/v) paraformaldehyde and antigen presentation assessed by incubating the cells with RF33.70 T-cell hybridoma and determining the IL-2 content of harvested medium using ELISA. Panel B: Assessment of the kinetics of class I peptide presentation. JAWSII cells were incubated with EtxB-conjugates for the indicated time intervals, fixed with 1% (w/v) paraformaldehyde and antigen presentation was assessed as above. Duplicate samples were tested and the data given as mean.+−.SD.

Figure 9:
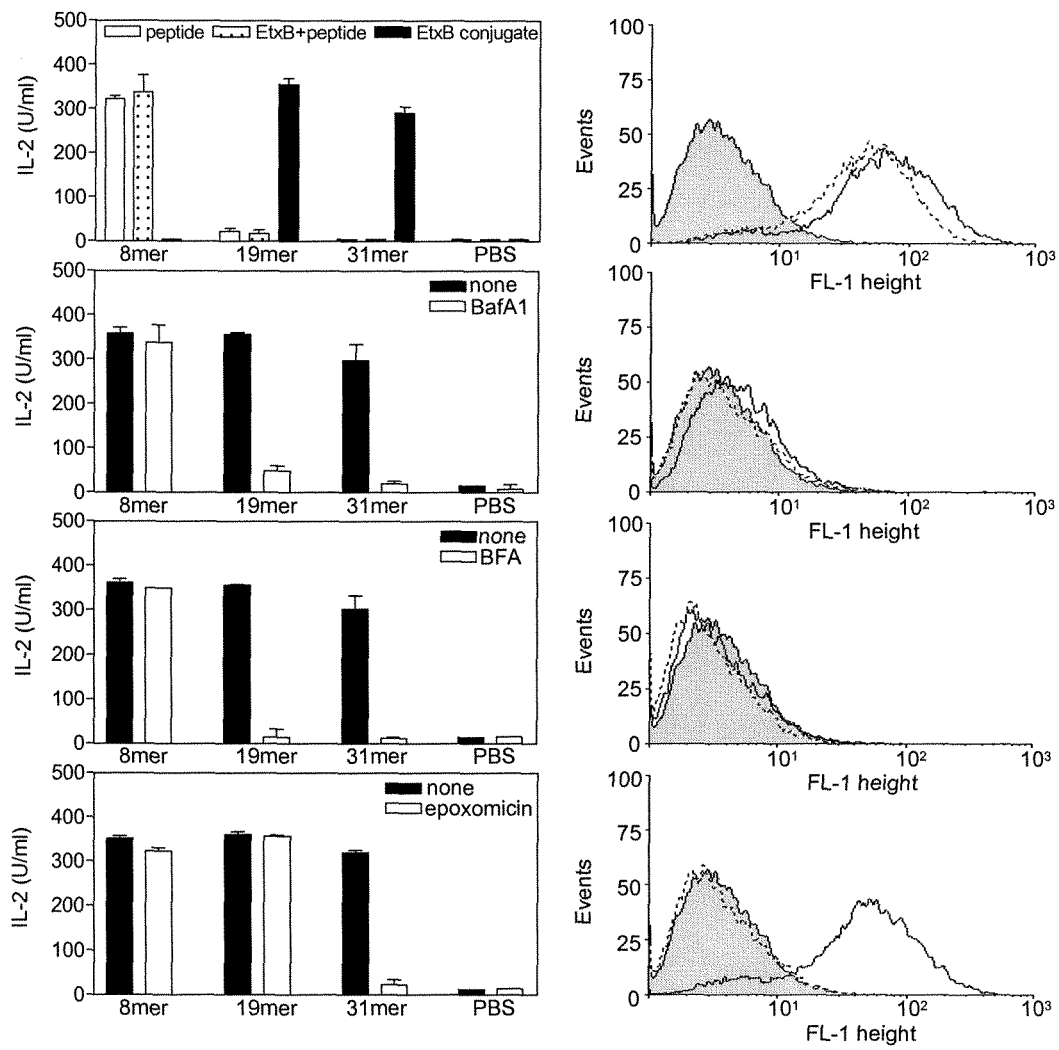

FIG. 9: Effect of inhibitors on EtxB-mediated delivery and presentation of class I peptides. The effects of 200 nM Bafilomycin A1 (BafA1), 10 μM Brefeldin A (BFA), and 10 μM epoxomicin on EtxB-mediated delivery of the 19mer (SEQ. ID NO: 7) and 31 mer peptide (SEQ. ID NO: 10) were assessed in both IL-2 release assays (Panel A-D) and FACS analysis using the 25D1.16 antibody (Panel E-H). Unconjugated 8mer peptide (SEQ. ID NO: 4) and PBS were used as positive and negative controls, respectively. IL-2 release data are given as mean.+−.SD. In panels D-F, EtxB-19mer (SEQ. ID NO: 15-SEQ. ID NO:7) (solid black curve), EtxB-31mer (SEQ. ID NO: 15-SEQ. ID NO:10) (dashed black curve), and PBS (grey filled curve) are shown.

Figure 10:
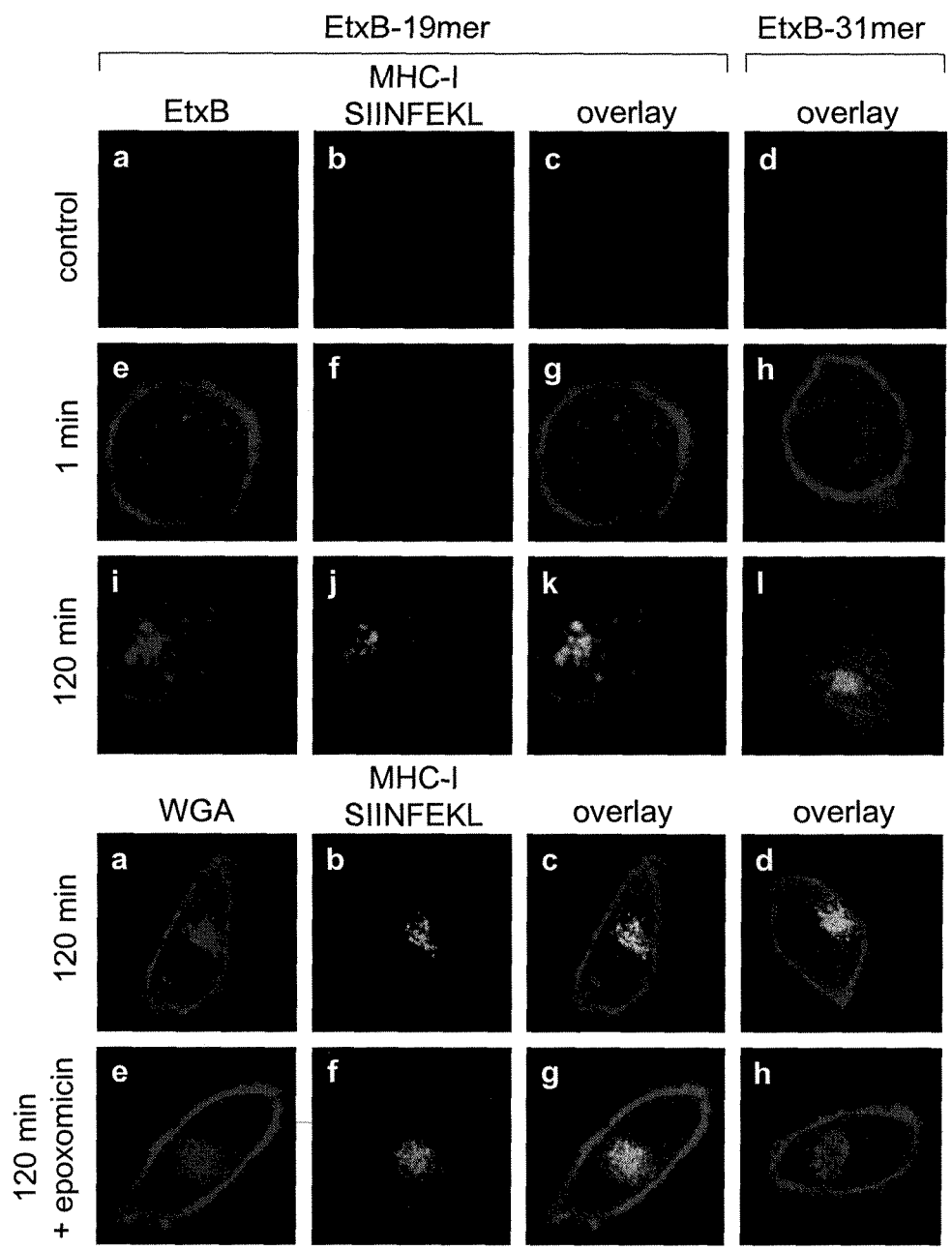

FIG. 10: EtxB-mediated delivery of class I peptides: Evidence for trafficking into the Golgi compartment and proteasome involvement. Panel A: Confocal microscopic analysis of the cellular localisation of EtxB (SEQ. ID NO: 15) and MHC-I/SIINFEKL (SEQ. ID NO: 4) complexes upon treatment of JAWSII cells with EtxB-19mer (SEQ. ID NO: 15-SEQ. ID NO:7) for 1 min (image e-g) or 120 min (image i-k), or with EtxB-31 mer (SEQ. ID NO: 15-SEQ. ID NO:10) for 1 min (image h) or 120 min (image 1). Control cells were treated with PBS for 120 min (image a-d). All cells were fixed with paraformaldehyde, and stained with a polyclonal rabbit antiserum specific for EtxB (SEQ. ID NO: 15), and the 25D1.16 mAb specific for MHC-I/SIINFEKL-complexes, followed by FITC- or TRITC-conjugated secondary antibodies as described in Materials & Methods. Cell nuclei were stained with DAPI (blue). For EtxB-19mer (SEQ. ID NO: 15-SEQ. ID NO: 7) both separate and overlayed images are shown whereas for the EtxB-31 mer (SEQ. ID NO: 15-SEQ. ID NO: 10) only the overlayed image is shown. Panel B: Co-localisation of MHC-I/SIINFEKL (SEQ. ID NO: 4) complexes with wheat germ agglutinin (WGA) and the effect of epoxomicin, a proteasome inhibitor on MHC-I loading. Cells were treated for 120 min with EtxB-19mer (SEQ. ID NO: 15-SEQ. ID NO: 7) (image a-c) or EtxB-31 mer (SEQ. ID NO: 15-SEQ. ID NO: 10) (image d) as above, fixed with paraformaldehyde followed by incubation with rhodamine-labelled WGA and mAb 25D1.16 and a FITC-labelled secondary antibody. For EtxB-19mer (SEQ. ID NO: 15-SEQ. ID NO: 7) both separate and overlayed images are shown whereas for the EtxB-31 mer (SEQ. ID NO: 15-SEQ. ID NO: 10) only the overlayed image is shown. An identical experiment to that shown in images a-d above was carried out with 10 μM epoxomicin added to the cells 60 min prior to addition of the EtxB-conjugates (image e-h).

Figure 11:
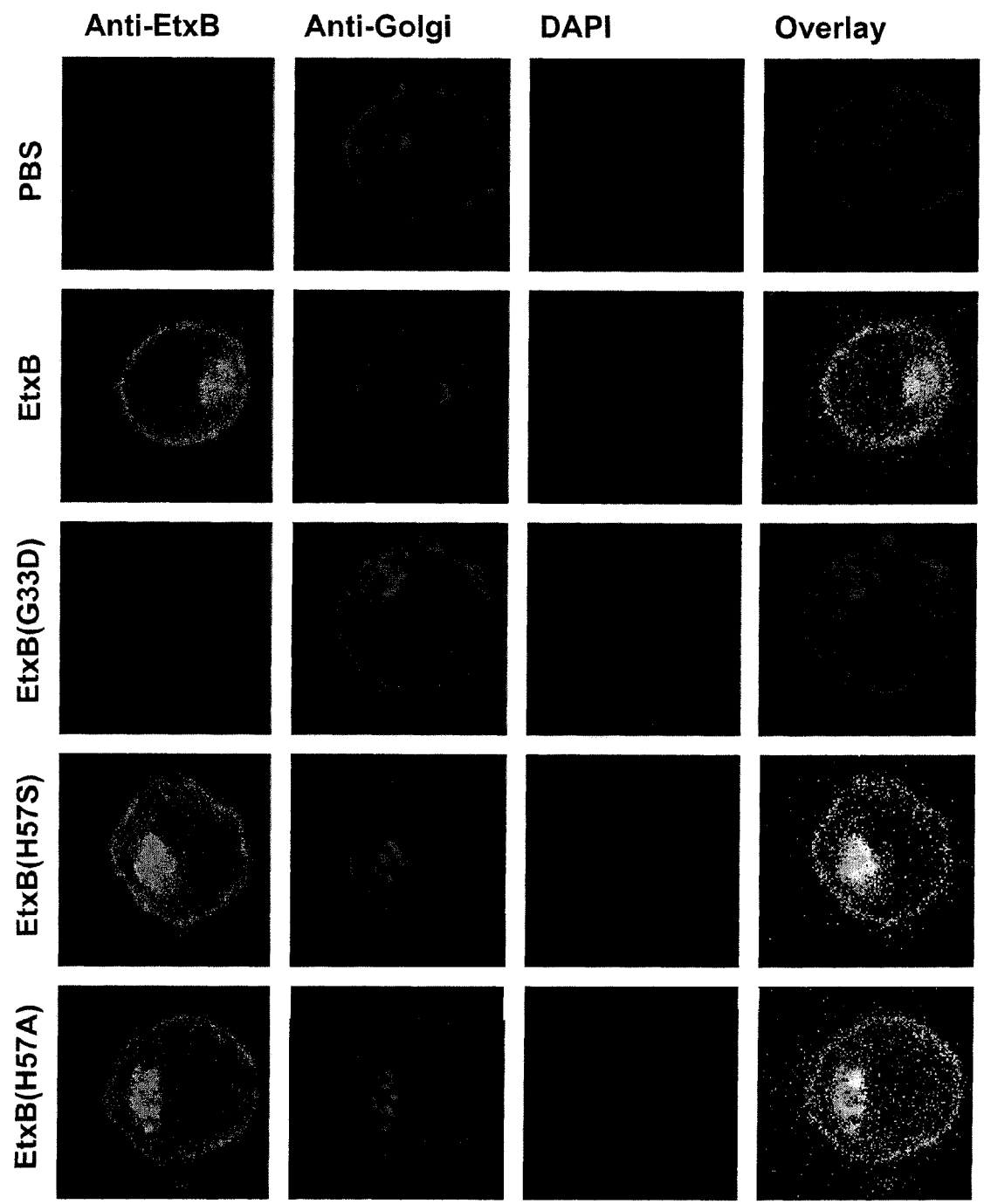

FIG. 11: FIG. 11 shows uptake of wild-type EtxB (SEQ. ID NO: 15) and two mutants EtxB(H57A) (SEQ. ID NO: 16) and EtxB(H57S) (SEQ. ID NO: 19) into Jurkat T-cells. In addition and as a control, a mutant which does not bind to GM1 at all, EtxB(G33D) (SEQ. ID NO: 14) was tested. Cells were stained with an antibody against the B-subunit (anti-EtxB), or with rodamine labelled wheat germ agglutinin (a marker for the Golgi-anti-Golgi), with the nuclear stain DAPI, and the images superimposed (right hand side). It is evident that EtxB (SEQ. ID NO: 15), EtxB(H57A) (SEQ. ID NO: 16), and EtxB(H57S) (SEQ. ID NO: 19) traffic into cells into a perinuclear compartment that co-localises with the Golgi marker wheat germ agglutinin. Thus, it is clear that EtxB(H57A) (SEQ. ID NO: 16) and EtxB(H57S) (SEQ. ID NO: 19) are capable of functioning as drug targeting molecules even though they no longer retain their immunomodulatory properties.

Figure 12:
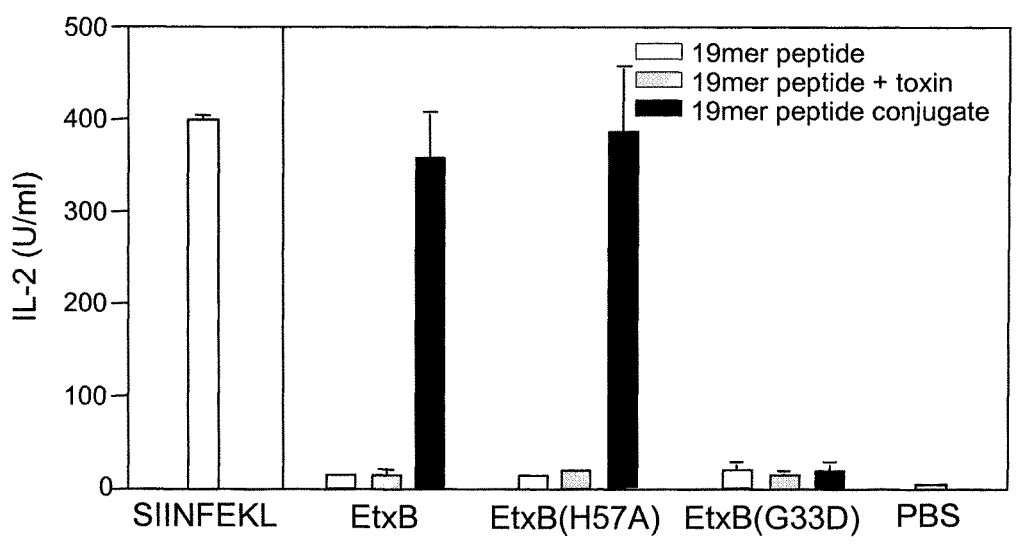

FIG. 12: EtxB(H57A) (SEQ. ID NO: 16) can be used as a peptide delivery vehicle. JAWS II dendritic cells were incubated for 2 hours with either a 19mer (CAVGAGATAEEESIINFEKL) peptide (SEQ. ID NO: 7) alone, the 19mer peptide (SEQ. ID NO: 7) admixed with either wild type EtxB (SEQ. ID NO: 15), EtxB(H57A) (SEQ. ID NO: 16) or the non-binding EtxB(G33D) (SEQ. ID NO: 14), or conjugates comprising EtxB-19mer (SEQ. ID NO: 15-SEQ. ID NO:7), EtxB (H57A)-19mer (SEQ. ID NO: 13-SEQ. ID NO: 7) or EtxB (G33D)-19mer (SEQ. ID NO: 14-SEQ. ID NO:7) at equivalent peptide concentrations of 100 nM. PBS and the 8mer (SIINFEKL) peptide (SEQ. ID NO: 4) alone were used as negative and positive controls. Cells were then fixed with 1% paraformaldehyde and incubated overnight with RF33.70 cells and the extent of peptide presentation assessed by analysis of IL-2 release into the culture medium. Duplicate samples were tested, and data are given as means SEM.

Materials & Methods

Part I—Example 1-5

Alanine-Scanning Mutagenesis and Gene Manipulation

Ala-substitutions were introduced into the V52 to I58 loop of CtxB (SEQ. ID NO: 12) by PCR mutagenesis (20). Plasmid pATA14 (21), a pBluescript IIKS derivative containing a reconstructed ctxB (SEQ. ID NO: 12) operon with an engineered EcoRI site at the 3'-end of the ctxA gene, was used as a PCR template. PCR fragments, with appropriately engineered substitutions in ctxB (SEQ. ID NO: 12), were ligated into the EcoRI-SpeI sites of pATA14, thereby replacing the wild-type ctxB gene (SEQ. ID NO: 12) with a mutant allele. The resultant plasmids, pATA16 to pATA22, were confirmed by DNA sequencing to encode Ala substitutions at residues 52 to 58 in CtxB (SEQ. ID NO: 12), respectively.

Plasmid pCDR3, was constructed by subcloning the EcoRV-SpeI fragment containing the entire ctxAB operon of pATA14, into the controlled expression vector pTTQ18 (21).

To facilitate subsequent purification and characterisation of wild-type and mutant B-subunits (devoid of any A-subunit), the ctxB gene (SEQ. ID NO: 12) from pATA14 and the mutant ctxB allele of pATA21 were subcloned into EcoRI-SpeI digested pTRH64 (13), a broad host-range controlled expression vector derived from pMMB66EH (22). The resultant plasmids were designated pATA13 (encoding wild type CtxB (SEQ. ID NO: 12)) and pATA29 (encoding the mutant B-subunit, CtxB(H57A) (SEQ. ID NO: 13)).

Periplasmic Extraction

Periplasmic extracts from *E. coli* XL1-Blue (Strategene) harbouring plasmids pATA14, or pATA16 to pATA22 were prepared as described in (23) and immediately dialysed against Hank's balanced salt solution (HBSS; Sigma, Mo.) containing 10 mM HEPES pH 7.4, and then flash frozen and stored at −80.degree. C. prior to electrophysiologic analysis.

Purification of Proteins

Plasmids pCDR3 and pATA21 encoding Ctx holotoxin and Ctx holotoxin (with an H57A mutation in the B-subunit (Ctx (H57A)), respectively were electroporated into *V. cholerae* 0395NT (that contains an engineered chromosomal ctxB deletion) and the toxins purified as previously reported (21). Plasmids pATA13 and pATA29 encoding wild-type CtxB (SEQ. ID NO: 12) and CtxB(H57A) (SEQ. ID NO: 13) respectively were mobilised into the non-pathogenic *Vibrio* sp. 60 strain, and the B-subunits purified from the culture media using the method reported in (7). EtxB(G33D) (SEQ. ID NO: 14) was purified from *Vibrio* sp 60 (pTRH64) as reported previously (13). Purified B-subunit preparations were applied to a detoxigel column (Pierce), and the eluted fractions pooled, dialysed against PBS. Protein concentration determined as reported in (24) and LPS content shown to be to be >30EU mg-1 protein (Bio Whittaker).

Crystallographic Structure Determination

Crystals of CtxB(H57A) (SEQ. ID NO: 13) were grown from hanging drops by vapor diffusion equilibration against a well buffer solution containing 50 mM NaCl, 100 mM Tris-HCl pH 8.4 and 32% (w/v) PEG 5000. Drops consisted of 1 μl of protein at 3 mg/ml in 100 mM Tris-HCl pH 7.5, 1 μl 300 mM galactose. (β-d-galactopyranoside), and 1 μl well buffer. Crystals formed in space group $P2_12_12$ (a=101.4 Å b=114.7 Å c=45.6 Å) with one pentamer per asymmetric unit. Diffraction intensities to 2.0 Å resolution were measured from a single flash-frozen crystal using 12 keV radiation from APS beamline 191D and a 3K.times.3K CCD detector in binned mode. The initial crystallographic model consisted of the previously determined CtxB(H94R) structure ((25); PDB accession code 3chb) positioned by molecular replacement. After rigid body refinement of the constituent monomers, the model for residues 50-62 of each subunit was rebuilt manually. Iterative positional and B-factor refinement, alternating with manually refitting, yielded crystallographic residuals R=0.253, Rfree=0.317. At this point, difference density for bound galactose was clear in 2 of the 5 subunits. Continued refinement with incremental addition of discrete water molecules and 2 additional galactose molecules yielded a model with R=0.191, Rfree=0.252. The final stages of refinement included 446 discrete water molecules, 4 galactose molecules, and a riding-hydrogen model, yielding final crystallographic residuals R=0.179, Rfree=0.239 with excellent stereochemistry. The mean estimated standard uncertainty in atomic coordinates based on Cruickshank's DPI measure was 0.19 Å. Intensity data were merged and scaled using programs denzo, scalepack, and truncate (26, 27). Model fitting and real-space optimization used the program Xfit (28), while is all remaining refinement used the program Refinac (27). Figures were prepared using programs MSMS (29) and Raster3D (30). The final model has been deposited with the Protein Data Bank, accession code 1 g8z.

Electrophysiology

T84 cells (from passage 80) obtained from the ATCC were grown and passaged as described (31). Toxins were diluted in prewarmed Hank's balanced salt solution (HBSS; Sigma, Mo.) and 10 mM HEPES pH 7.4, and applied to the apical surface of confluent T84 cell monolayers in Transwell inserts (Costar, Cambridge, Mass.), followed by incubation at 37.degree. C. Measurements of short circuit current ($I_{sc}$) and resistance (R) were performed as reported elsewhere (31).

Toxin-Receptor Interaction

GM1-enzyme linked immunosorbent assay. Toxin B-subunit interaction with GM1 was monitored on microtiter plates (Immulon 1, Dynatech, USA) coated with 1.5 μg/ml GM1 (Sigma) in PBS as reported previously (13), using LT39 (32), a monoclonal antibody that detects both CtxB (SEQ. ID NO: 12) and EtxB (SEQ. ID NO: 15), or 118-8, a monoclonal antibody that detects EtxB (33).

Surface plasmon resonance. Liposomes were prepared from 2 ml of 5 mole % GM1: 95 mole % 1-palmitoyl-2-oleoyl-sn-glycero-3-phosphocholine (POPC) in choloroform-methanol (2:1). The glycolipid:lipid mixture was allowed to evaporate under vacuum and then dissolved in PBS and passed through a polycarbonate filter (50 nm pore size) using the LipoFast Basic System (Avestin Inc., Glen Creston Ltd, Middlesex, England) as recommended by the manufacturer and described by Kuziemko et al. (1996). A BIAcore 1000 (Pharmacia) was employed to coat an HPA sensor chip (Biocore, Herts, England) with GM1-containing liposomes, and B-subunit $K_D$ binding measurements were obtained as reported previously (34).

Lymphocyte Isolation and Culture

Mesenteric lymph nodes and spleens were removed from 6-10 week old NIH mice bred under SPF conditions (University of Bristol) and the tissues crushed under wire mesh. The cells were then washed three times in Hanks medium without calcium and magnesium (Gibco BRL)+20 mM HEPES (Sigma-Aldrich). Red blood cells were lysed by the addition of 0.5 ml Ack Lysing buffer (Bio Whittaker) for 30 seconds. For the purification of specific lymphocyte populations, cells were washed in PBS containing 0.5% (w/v) BSA and 5 mM EDTA (BDH laboratory supplies, Poole), prior to the addition of specific antibodies conjugated with MACS microbeads (Miltenyi Biotec, Germany) for 35 min on ice. CD8+ T-cells were negatively selected using anti-CD4 and anti-B220. B-cells were negatively selected using anti-CD43. Labelled cell suspensions were applied to VS selection columns (Miltenyi Biotec) and the negative fractions eluted with 0.5% (w/v) BSA-PBS containing 5 mM EDTA and used immediately.

MLN cells, purified CD8+ T-cells and B-cells were cultured at 37.degree. C. in 5% CO2 at a concentration of $2 \times 10^6$/ml in α-modified Eagles Medium (Gibco) for MLN and CD8+ T-cells and RPMI 1640 medium (Gibco) for B-cells, both supplemented with 20 mM HEPES, 4 mM L-glutamine, 100 IU/ml penicillin, 100 μg/ml Streptomycin, $5 \times 10^{-5}$ M 2-Mercaptoethanol and 5% (v/v) foetal calf serum (Sigma). MLN and B-cells were cultured for 48 hours, or CD8+ T-cells for 18 h, in the absence or presence of either wild-type or mutant B subunits at the concentrations specified. In some experiments, treated cells were resuspended in Hanks medium supplemented with 20 mM HEPES 0.02% (w/v) sodium azide, 10% (v/v) rat serum and either incubated for 30 min on ice with rat anti-mouse CD8α-PE (PharMingen) and rat anti-mouse CD4-FITC (PharMingen) or stained with propidium iodide (Sigma) and then analysed by flow cytometry, as previously described (14).

Immunfluorescent Staining

Isolated CD8+ T-cells ($2 \times 10^6$ were incubated on ice in PBS with 100 nM wildtype or mutant B subunits for 1 hour. Treated cells were analysed by immunofluorescence microscopy and flow cytometry to detect bound B-subunit. For immunofluorescence microscopy, treated cells were washed in ice cold PBS, overlaid onto cover slips pre-coated with poly-L-lysine (Sigma), fixed (3.7% (v/v) formaldehyde, 4.degree. C., 4 min; methanol, -20.degree. C., 5 min) and labelled with anti-EtxB or anti-CtxB antibodies, followed by FITC-goat anti-mouse IgG (DAKO A/S Denmark). The cover slips were mounted using Mowiol mounting medium+2.5% (w/v) DABCO (Sigma) and analysed using a Zeiss Axioskop fluorescence microscope. In a parallel experiment the cells were labelled with the same antibodies and analysed by flow cytometry.

Immunizations

Anti-CtxB responses in NIH mice following subcutaneous immunization with either $2 \times 30$ μg of B-subunit (SEQ. ID NO: 12) or intranasal immunization with $3 \times 10$ μg B-subunit (SEQ. ID NO: 12) were determined by using GM1-microtiter plates coated with 1 μg/ml CtxB (SEQ. ID NO: 12) as reported previously (13).

Example 1(a)

Alanine Scanning Mutagenesis of the Conserved V52 to I58 Loop in Cholera Toxin B-Subunit (SEQ. ID NO: 12). Residues V52 to I58 of the B-subunit of cholera toxin (SEQ. ID NO: 12) were subjected to alanine scanning mutagenesis to assess whether this region, which comprises a conserved, flexible loop, plays an important role in cholera toxin action. To facilitate the construction and analysis of the various mutant Ctx proteins, the ctxA and ctxB genes (SEQ. ID NO: 12) were firstly PCR amplified as separate cistrons and then ligated to reconstruct a ctx operon with a conveniently situated EcoRI site at the fusion junction. As a consequence, a Lys to Arg substitution was introduced at residue 237 in the mature CtxA-subunit resulting in an alteration in the C-terminal-KDEL sequence, to yield –RDEL (which is identical to the C-terminus normally found in the A-subunit of *E. coli* enterotoxin).

Results 1(a)

This substitution in CtxA was demonstrated not to alter the A-subunit's intrinsic ADP-ribosyltransferase activity or the kinetics and magnitude of toxin-induced Cl-secretion in polarized T84 epithelial cells (21).

Example 1(b)

Plasmid pATA14, encoding CtxA$^{(RDEL)}$CtxB (hereafter referred to as Ctx), was subjected to site-directed mutagenesis to introduce individual Ala substitutions at residues from V52 to I58 in CtxB (SEQ. ID NO: 12), as described in the Materials & Methods.

Results 1(b)

When crude periplasmic extracts from *E. coli* strains expressing these mutant Ctx toxins were evaluated for their capacity to induce Cl-secretion by T84 cells it was found that one of the mutants containing a His to Ala substitution at residue 57 had an apparent severe toxicity defect (see below).

Example 1(c)

To further investigate this and in particular to evaluate the impact of the HS7A mutation on B-subunit function, both the mutant holotoxin, Ctx(H57A) and recombinant B-subunits, CtxB(HS7A), devoid of contaminating A-subunit, were purified and their identity confirmed by mass spectrometry.

Results 1(c)

Prior to assessing the functional properties of the mutants (SEQ. ID NOS: 13, 14, 17, 18 & 19), we showed that the intrinsic stability of the CtxB(H57A) (SEQ. ID NO: 13) pentamers were, like wild-type CtxB (SEQ. ID NO: 12), remarkably stable, retaining their oligomeric structure at pH's as low as 3.0 or when incubated in presence of 1% (w/v) of the ionic detergent, sodium dodecyl sulphate (data not shown).

Example 2

Ctx(H57A) Exhibits a Severe Defect in Toxicity Purified preparations of both wild-type Ctx and Ctx(H57A) were tested for their ability to trigger chloride efflux in polarised human intestinal epithelial (T84) cells (FIG. 1).

Results 2

Addition of 2 nM Ctx to the apical surface of T84 cells resulted in a characteristic 40 min lag period followed by rapid and maximal Cl-efflux, as monitored by a change in short circuit current across the cell monolayer. By contrast, the addition of an equimolar concentration of Ctx(H57A) to T84 cells failed to trigger Cr efflux suggesting that the His-57 residue plays a vital role in cholera toxin action (FIG. 1). The mutant displayed an almost complete lack of toxicity even at concentrations of 1000 nM (data not shown).

Example 3

CtxB(H57A) (SEQ. ID NO: 13) Retains the Ability to Bind to GM1 and to the Surface of Mammalian Cells Example 3(a)

Given that the mutation is adjacent to the receptor-binding pocket in the B-subunit, one possible explanation for the toxicity defect was that the mutant (SEQ. ID NO: 13) had lost the ability to bind with high affinity to GM1-ganglioside. The binding of CtxB(H57A) (SEQ. ID NO: 13) to GM1 was evaluated by both ELISA and surface plasmon resonance.

Results 3(a)

Figure 2:
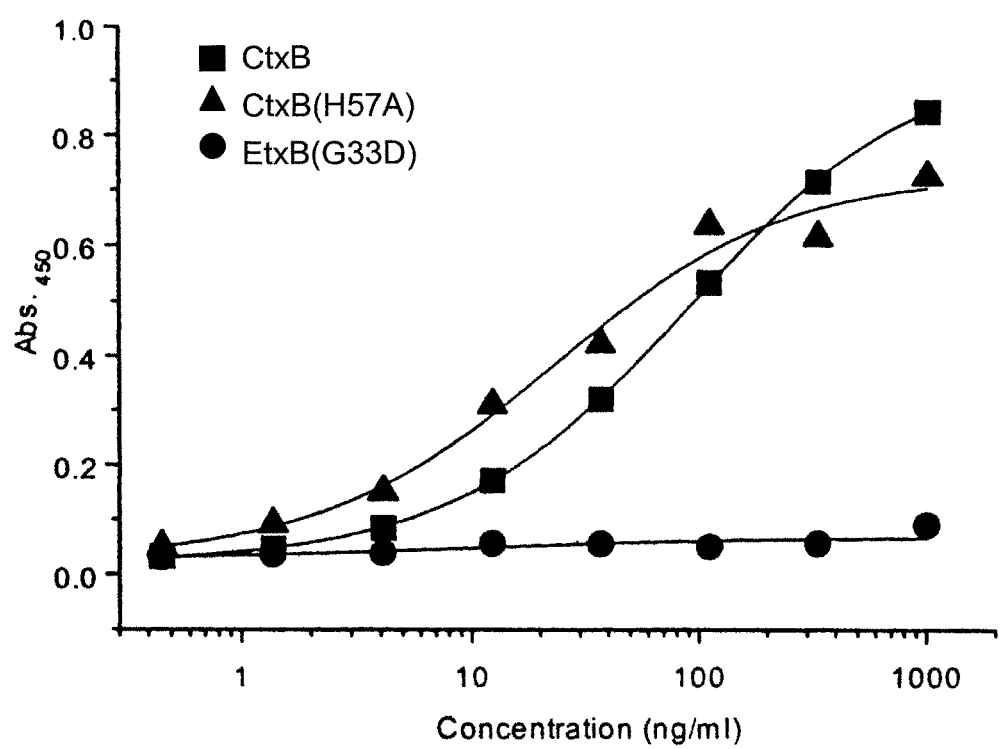

Microtiter plates coated with GM1 were incubated with various concentrations of CtxB (SEQ. ID NO: 12), CtxB (H57A) (SEQ. ID NO: 13) and EtxB(G33D) (SEQ. ID NO: 14) and bound protein detected using anti-B-subunit monoclonal antibodies (FIG. 2). CtxB (SEQ. ID NO: 12) and CtxB(H57A) (SEQ. ID NO: 13) bound to GM1-coated microtiter plates to a similar extent, with the sensitivity of detection for both subunits being in the 1-2 ng/ml range (equivalent to $1.6\text{-}3.2 \times 10^{-11}$ M). The $K_D$ for interaction with GM1 was determined by surface plasmon resonance using the method of Kuziemko et al (1996) and found to be $1.9\ (.+-.0.9) \times 10^{-10}$ M for CtxB (SEQ. ID NO: 12) and $5.0\ (.+-.3.7) \times 10^{-10}$ M for CtxB(H57A) (SEQ. ID NO: 13). We therefore conclude that CtxB(H57A) (SEQ. ID NO: 13) retains a very high avidity for interaction with GM1.

Example 3(b)

Figure 3:
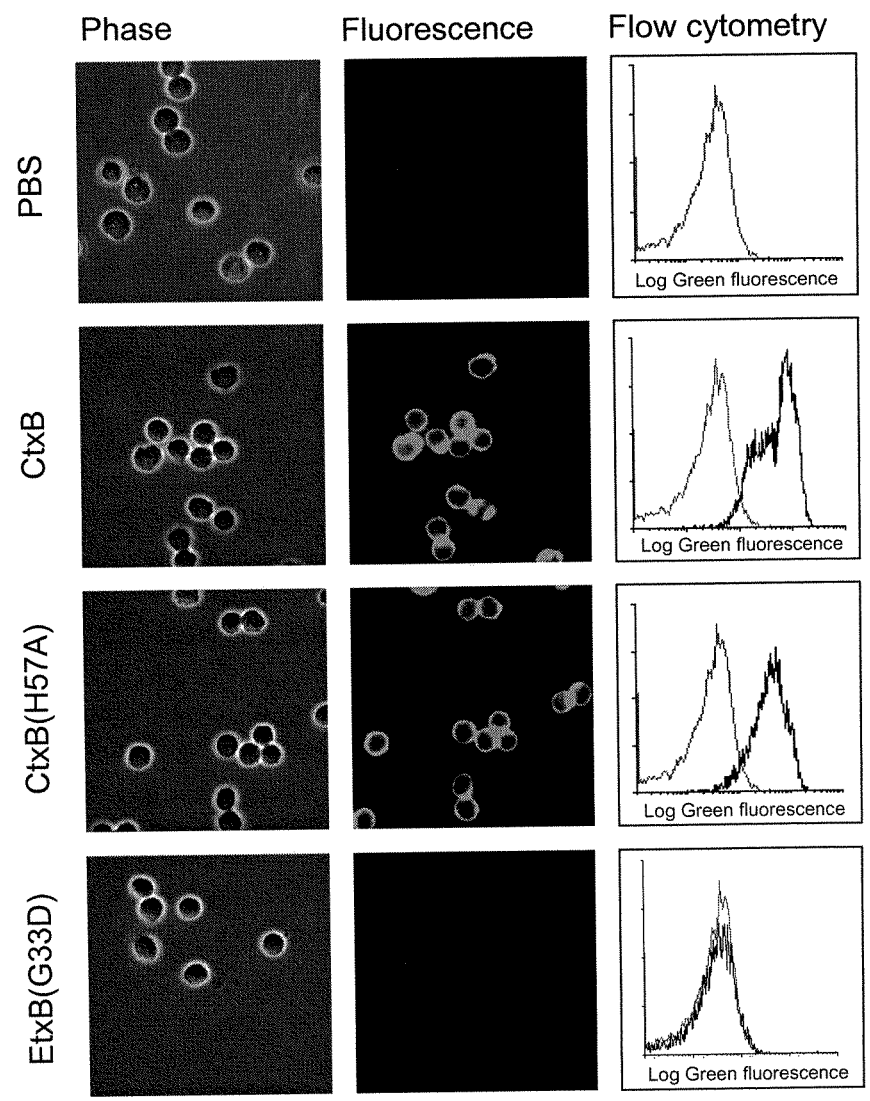

To further investigate aspects of the function of CtxB (H57A) (SEQ. ID NO: 13) we assessed whether it could bind to mammalian cells. For this purpose we selected murine CD8+ T-ells, as these had previously been shown to be suitable for assessing CtxB (SEQ. ID NO: 12) and EtxB (SEQ. ID NO: 15)-mediated effects on immune cells (14). Highly purified CD8+ T-cells from the mesenteric lymph node (MLN) of NIH mice were incubated on ice with 100 nM of CtxB (SEQ. ID NO: 12), CtxB(H57A) (SEQ. ID NO: 13) or EtxB(G33D) (SEQ. ID NO: 14) and the bound B-subunits detected using anti-B-subunit antibodies and a FITC secondary antibody, prior to analysis by fluorescence microscopy (FIG. 3A) or flow cytometry (FIG. 3B).

Results 3(b)

Microscopy revealed a clear halo of fluorescence around the cells incubated with both CtxB (SEQ. ID NO: 12) and CtxB(H57A) (SEQ. ID NO: 13) but not with EtxB(G33D) (SEQ. ID NO: 14) or cells incubated with PBS. Flow cytometry permitted a semi-quantitative measurement of B-subunit binding to the cells, since the fluorescence detected by the FACscan is directly proportional to the amount of bound secondary antibody. When control samples, using cells incubated in PBS were analysed by the FACScan, low level background fluorescence was detected and is shown as the red line in FIG. 3B. Incubation with CtxB (SEQ. ID NO: 12), CtxB (H57A) (SEQ. ID NO: 13), but not with EtxB(G33D) (SEQ. ID NO: 14), resulted in a marked increase in fluorescence intensity, indicative of B-subunit binding to CD8+ T-cells (FIG. 3B; black line). In addition, when concentrations as low as 1-10 nM were tested no difference in the relative fluorescence shifts between wild-type CtxB (SEQ. ID NO: 12) and CtxB(H57A) (SEQ. ID NO: 13) were observed. We therefore conclude that CtxB(H57A) (SEQ. ID NO: 13) retains a high affinity for GM1 and shows a comparable level of binding to mammalian cells as wild-type CtxB (SEQ. ID NO: 12).

Example 4

CtxB(H57A) (SEQ. ID NO: 13) Lacks Immunomodulatory Activity

Example 4(a)

An unexpected property of CtxB (SEQ. ID NO: 12) and EtxB (SEQ. ID NO: 15) is their capacity to induce the selective apoptosis of murine CD8+ T-cells, involving an NF.kappa.B-dependent and caspase-3 dependent pathway ((14); This has previously been proposed to be dependent on B-subunit interaction with GM1, since EtxB(G33D) (SEQ. ID NO: 14) fails to elicit such an effect (14). CtxB(H57A) (SEQ. ID NO: 13) was therefore tested to assess if it had retained the capacity to induce CD8+ T-cell apoptosis. MLN cells were cultured for 48 h in the presence or absence of 100 nM CtxB (SEQ. ID NO: 12), CtxB(H57A) (SEQ. ID NO: 13) or EtxB (G33D) (SEQ. ID NO: 14), then the CD4+ and CD8+ T-cells stained with fluorescently labelled antibodies and detected by flow cytometry.

Results 4(a)

Figure 4A:
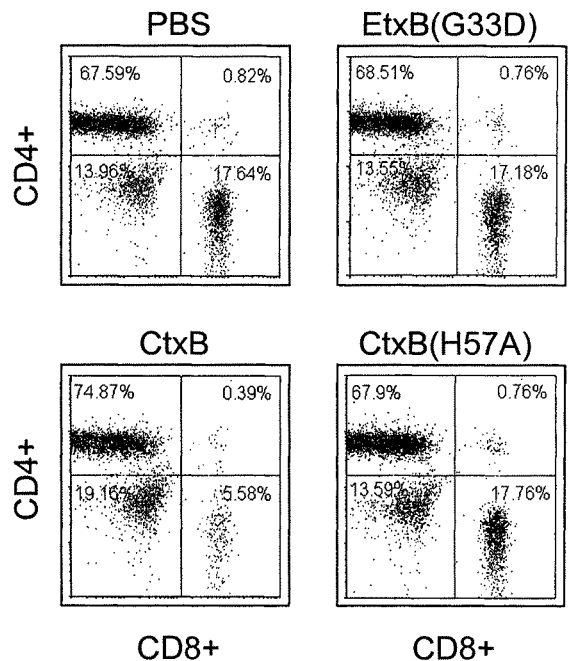

FIG. 4A shows that after 48 h, cells cultured with either PBS or the non-binding mutant EtxB(G33D) (SEQ. ID NO: 14) contained approximately 17-18% CD8+ T-cells, whilst treatment with wild type CtxB (SEQ. ID NO: 12) reduced the proportion of CD8+ T-cells to <6%. Strikingly, CtxB(H57A) (SEQ. ID NO: 13) failed to induce any CD8+ T-cell depletion above that seen for the negative controls.

Example 4(b)

Figure 4B:
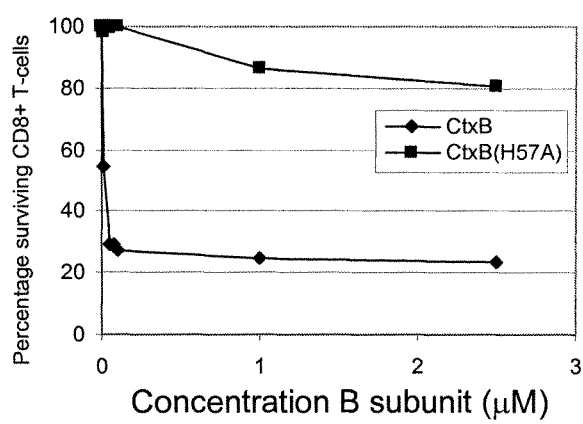

In order to investigate this further, MLN cell cultures were treated with concentrations of B-subunit (SEQ. ID NO: 12, 13 & 14) ranging from 10 nM to 2.5 µM and CD8+ T-cell depletion assessed as before (FIG. 4B).

Results 4(b)

This revealed that 100 nM CtxB (SEQ. ID NO: 12) resulted in maximal CD8+ T-cell depletion whereas even at the highest concentration of 2.5 µM, CtxB(H57A) (SEQ. ID NO: 13) showed only a modest capacity to induce depletion.

Example 4(c)

High doses of the B subunits (SEQ. ID NOS: 12, 13 & 14) (3.45 µM) were also tested for their capacity to induce apoptosis in isolated CD8+ T-cells derived from the MLN. The cells were cultured for 18 h in the presence or absence of the B-subunits (SEQ. ID NOS: 12, 13 & 14), and then stained with propidium iodide to reveal levels of sub-diploid DNA, indicative of apoptotic cells.

Results 4(c)

Figure 4C:
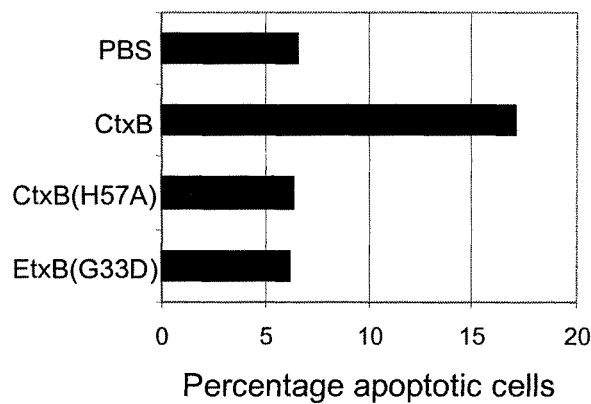

FIG. 4C shows that wild-type CtxB (SEQ. ID NO: 12), but not CtxB(H57A) (SEQ. ID NO: 13) or EtxB(G33D) (SEQ. ID NO: 14) increased the percentage of apoptotic cells above background. We therefore conclude that, even though CtxB (H57A) (SEQ. ID NO: 13) binds to CD8+ T-cells, it nonetheless exhibits a severe defect in inducing their apoptosis.

Example 4(d)

In addition the effect of CtxB (SEQ. ID NO: 12) and the mutant B-subunits (SEQ. ID NOS: 13 & 14) on activation of B-cells was investigated as it has been reported that CtxB (SEQ. ID NO: 12) and EtxB (SEQ. ID NO: 15) cause the up-regulation MHC Class II and CD25 (11, 12).

Results 4(d)

As expected, 48 h treatment of isolated splenic B-cells with 1.75 µM CtxB (SEQ. ID NO: 12) increased surface-expression of MHC Class II and CD25, whereas CtxB(H57A) (SEQ. ID NO: 13) or EtxB(G33D) (SEQ. ID NO: 14) did not.

Example 4(e)

To investigate if the defect in modulation of immune cells in vitro correlated with a corresponding loss in potent immunogenicity in vivo, mice were immunised subcutaneously or intranasally with CtxB (SEQ. ID NO: 12) or CtxB(H57A) (SEQ. ID NO: 13) as described in the Materials & Methods.

Results 4(e)

Subcutaneous immunisation with 30 μg CtxB (SEQ. ID NO: 12) or CtxB(H57A) (SEQ. ID NO: 13) in PBS, on two occasions 10 days apart resulted in a 78-fold difference in mean serum anti-B-subunit IgG titers of 7000.+−.1800 and 90.+−.90, respectively. If mice were given three 10 μg intranasal doses of CtxB (SEQ. ID NO: 12) or CtxB(H57A) (SEQ. ID NO: 13) in PBS, on three occasions 7 days apart, the mean serum anti-B-subunit titers were 125000.+−.64000 and 11000.+−.3000, respectively. We therefore conclude that the H57A mutation (SEQ. ID NO: 13) causes a marked reduction in B-subunit immunogenicity.

Example 5

X-Ray Crystallographic Structure of CtxB(SEQ. ID NO: 13)

To gain an insight into the structural consequences of substituting His-57, CtxB(H57A) (SEQ. ID NO: 13) was co-crystallized with galactose.

Results 5

Figure 5A:
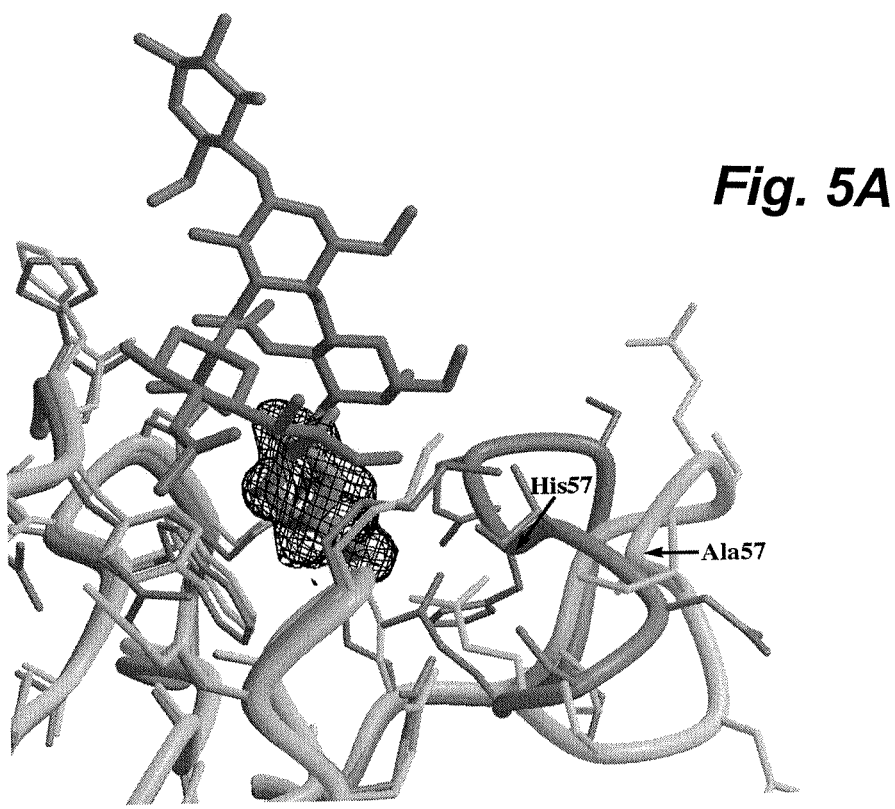
Figure 5B:
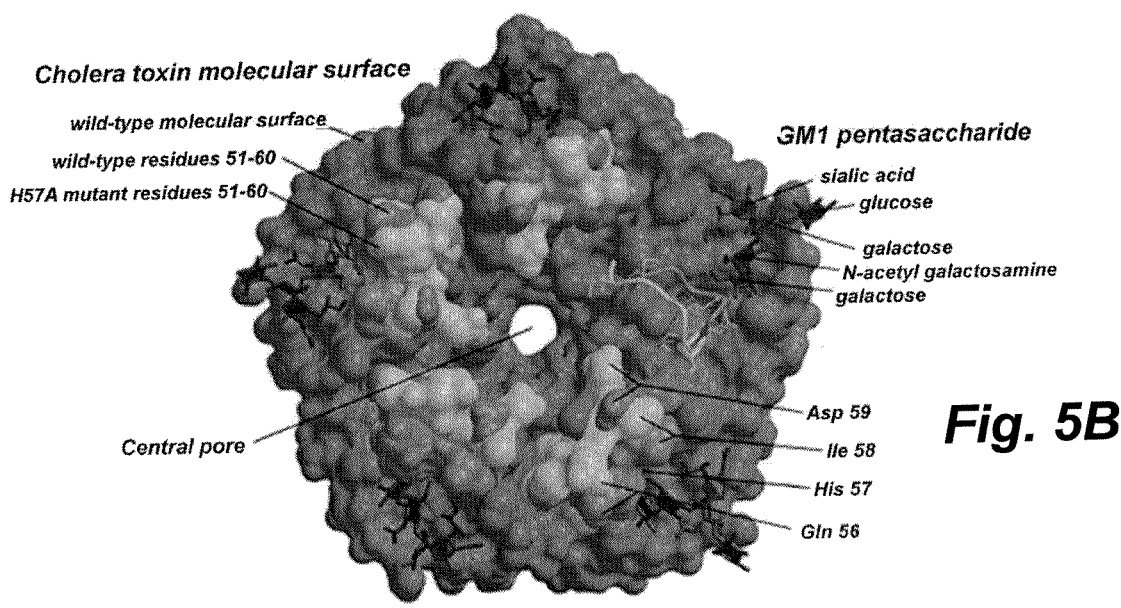

This revealed an X-ray structure that is remarkable in several respects. The most striking alteration is the conformation of the V52-I58 loop in CtxB(H57A) (SEQ. ID NO: 13) which is quite different from that found in the wild-type toxin (FIGS. 5A and B). The $C^\alpha$ atom of the mutated residue 57 is shifted by .about.4 Å, and the difference in the backbone position increases to .about.7 Å at residue Gln-56 in comparison with the structure of wild-type CtxB (SEQ. ID NO: 12) complexed with GM1-oligosaccharide (GM1-OS) (18, 25). Moreover, the shift is observed in all 5 subunits even though galactose is bound only to 4 of them. The net effect of the conformational change is to displace residues 52-58 towards the central pore of the toxin B-pentamer, with the result that the accessible surface of the toxin pentamer is substantially altered in this region (FIG. 5B). In the wild-type CtxB (SEQ. ID NO: 12): GM1-OS complex both residues E-51 and Q-61 form direct hydrogen bonds with the terminal galactose of GM1, while residue Q-56 forms solvent-mediated hydrogen bonds with both the terminal galactose and the sialic acid of GM1. Given this, it is somewhat unexpected that such a large change in loop conformation does not disrupt, or at least perturb, sugar binding. Nevertheless, the observed galactose location in the present complex differs by only 0.4 Å r.m.s, from that seen for the terminal galactose in the GM1-OS complex (FIG. 5A). We therefore would predict that regardless of the displacement of the loop the overall GM1 binding mode is essentially unperturbed by the mutation (FIG. 5B), which is in accord with our biophysical measurements of GM1 affinity.

In addition to the shift in position of the loop, residues 52-58 are well-ordered in each of the five subunits of the CtxB(H57A) (SEQ. ID NO: 13) structure. In a large set of previous structures determined for CtxB (SEQ. ID NO: 12) and EtxB (SEQ. ID NO: 15) in complex with various receptor analogues there has been a near-perfect correlation of order with sugar binding (19). This has been interpreted as implying that the loop is relatively flexible in the unbound toxin, becoming well-ordered as it moulds itself around the terminal galactose sugar during receptor binding. In the mutant CtxB (H57A) (SEQ. ID NO: 13) structure this correlation is lost: implying that the transition of the loop from a disordered to a fixed structure, that occurs when wild-type B-pentamers bind to receptors, has already occurred in the H57 mutant (SEQ. ID NO: 13) in the absence of bound saccharide.

Materials and Methods

Part II—Examples 6-11

Experimental Protocols on how to Determine Whether Peptides Attached to EtxB (SEQ. ID NO: 15) are Delivered into the MHC Class I Pathway Production and Characterisation of EtxB (SEQ. ID NO: 15) and EtxB-Conjugates Recombinant EtxB was expressed in a non-toxinogenic vibrio, Vibrio sp. 60, and purified as reported earlier (15). EtxB (SEQ. ID NO: 15) was depleted of LPS using detoxi-gel columns (Pierce, Rockford), resulting in .Itoreq.50 endotoxin units (EU) per mg EtxB (SEQ. ID NO: 15), as determined in a *Limulus* amoebocyte lysate assay (BioWhittaker, Walkersville). Peptides were synthesised by solid phase synthesis and purified by reverse-phase HPLC by Dr. G. Bloomberg (Department of Biochemistry, University of Bristol). The molecular mass of each peptide was confirmed by mass spectrometry. The amino acid sequences and molecular weights of peptides used in this study are listed in Table 1.

TABLE 1

| Peptide | Sequence | $M_W$ | SEQ ID NO: |
|---|---|---|---|
| 8mer | SIINFEKL | 945 | 4 |
| 9mer | CSIINFEKL | 1048 | 5 |
| 16mer | CEKLAGFGSIINFEKL | 1751 | 6 |
| 19mer | CAVGAGATAEESIINFEKL | 1905 | 7 |
| 26mer | CEKLAGFGAVGAGATAESIINFEKL | 2608 | 8 |
| 26mer* | CEKLAGFGARGAGATAESIINFEKL | 2665 | 9 |
| 31mer | CEKLAGFGARGAGATAESIINFEKL | 3212 | 10 |

For conjugation of peptides to EtxB (SEQ. ID NO: 15) the chemical bifunctional cross-linker N-(gamma-maleimido-butyryl-oxy)succinimide (GMBS)(Pierce) was used. In brief, EtxB (SEQ. ID NO: 15) was first reacted with GMBS in a 1:4 molar ratio for 1 h at room temperature, and excess GMBS removed by gel filtration on a Sephadex G-25 column (Pharmacia, Uppsala, Sweden). Fractions containing EtxB-GMBS were pooled and reacted with peptide at a 1:2 molar ratio for 2 h at room temperature. Each peptide contained an N-terminal cysteine to allow direct reaction between the free cysteine and the second reactive group in the GMBS molecule. Unreacted GMBS groups were quenched by the addition of 2-mercaptoethanol (2-ME)(Sigma, Poole, UK) to a final concentration of 50 mM and incubation at room temperature for 30 minutes. Finally, EtxB-peptide conjugates were separated from excess peptide on a Sephadex G-50 column (Pharmacia). For all peptides, an EtxB pentamer:peptide ratio of approximately 1:5 was achieved, as estimated by gel filtration on a Superdex 200 column connected to a SMART system (Pharmacia), using molecular weight standards. Conjugate concentration was determined using the Dc protein assay (BioRad, Richmond), and the molar equivalent concentration of peptide estimated from the EtxB:peptide ratio. Conjugates were analysed either boiled or unboiled on SDS-polyacrylamide gels followed by staining with Coomassie. The immunoreactivity of conjugates was examined by Western blotting using a monoclonal antibody (mAb)(118-8) specific for EtxB pentamers and a polyclonal antiserum specific for the SIINFEKL peptide (a gift from Dr. Y. Reiss, Tel Aviv University, Israel). The GM1-binding properties of EtxB (SEQ. ID NO: 15) and EtxB-conjugates were assessed in a GM1-sandwich ELISA, essentially as previously described (15).

Cell Lines and Culture Conditions

JAWSII, an immortalised C57BL/6 bone marrow-derived dendritic cell line (U.S. Pat. No. 5,648,219), was purchased from the American Type Culture Collection (Manassas), and cultured in RP10 medium (RPMI 1640 containing Glutamax-1,100 µg/ml penicillin/streptomycin and 10% foetal bovine serum (FBS)(all from GIBCO BRL, Paisley, UK)) supplemented with 2 ng/ml recombinant mouse GM-CSF (Sigma) at 37.degree. C. in a humidified CO2 incubator. T-cell hybridoma RF33.70 (16), recognising the OVA(257-264) SIINFEKL peptide in the context of H-2 $K^b$ MHC-I, was a kind gift from Dr. K. L. Rock (University of Massachusetts), and was cultured as above in RP10 medium containing 20 mM HEPES, 1 mM non-essential amino acids, 25 µM indomethacin, 0.25 µm fungizone one (all from GIBCO), and 5.times.$10^{-5}$ M 2-ME.

Antigen Presentation Assays

Peptide presentation by MHC-I was examined by monitoring IL-2 release by the RF33.70 T-cell hybridoma (16). JAWSII dendritic cells were seeded in 96 well plates at 2.times.$10^5$ cells/ml and cultured overnight. Cells were then incubated with duplicate test samples at the concentrations and for the time intervals indicated. In all experiments equivalent amounts of either free or conjugated peptide were used. After incubation with antigen cells were fixed with 1% paraformaldehyde for 10 min at room temperature, washed 5.times. with medium, and incubated overnight with RF33.70 T-cell hybridoma (5×$10^5$ cells/ml). Free 8mer SIINFEKL peptide (SEQ. ID NO: 4) and PBS were used as positive and negative controls, respectively. After overnight incubation, presentation-induced IL-2 secretion was determined using a commercially available IL-2 ELISA kit (Pharmingen, San Diego). IL-2 levels are given as mean U/ml.+-.standard deviation (SD). Presented data are representative of at least 3 independent experiments.

An alternative FACS-based method for a direct assessment of antigen presentation by JAWSII cells, involving the use of the 25D1.16 mAb directed against the MHC-I/SIINFEKL complex (17) (kindly donated by Drs C. Reis e Sousa, Imperial Cancer Research Fund, UK) was also used to assess EtxB-mediated class I presentation. In brief, 2-4×$10^6$ JAWSII cells were treated with peptide or EtxB (SEQ. ID NO: 15) alone or admixed, or EtxB-conjugate at the equivalent concentration of 100 nM peptide for 2 h in a 25 cm2 tissue culture flask. Cells were then trypsinised, centrifuged (5 min, 1000 rpm), washed with PBS/FBS/azide (PBS containing 5% FBS, and 0.02% sodium azide), and incubated with 25D1.16 mAb (1:200), 30 min, 4.degree. C. Subsequently, cells were washed with PBS/azide, and incubated with a FITC-labelled goat antibody specific for mouse IgG (1:500)(DAKO, Cambs, UK), 30 min, 4.degree. C. Finally, cells were washed with FACS flow (Becton Dickinson, San Jose), and analysed by flow cytometry (FACScan; Becton Dickinson). SIINFEKL peptide-treated and untreated cells were used as controls.

The inhibitory effects of Bafilomycin A1 (BafA1), Brefeldin A (BFA)(both from Sigma), and epoxomicin (Calbiochem, Nottingham, UK) on EtxB-mediated delivery were also studied. In such experiments, JAWSII cells were pre-incubated with inhibitors for 1 h at indicated concentrations. Subsequently, cells were incubated with EtxB-conjugates or EtxB (SEQ. ID NO: 15) and peptide alone or admixed for 2 h and processed as above.

Confocal Microscopy

For microscopic analysis JAWSII cells were first grown for 48 h on sterile cover slips coated with rat collagen type II (Sigma). Subsequently, cells were treated for indicated periods of time with EtxB-conjugates, fixed with 4% paraformaldehyde for 10 min, and then permeabilised by a 15 min incubation in 4% paraformaldehyde containing 0.5% Triton X-100 (Sigma). After repeated washing with PBS, cells were incubated with either mAb 25D1.16, specific for the MHC-I/SIINFEKL complex (1:200), or an EtxB-specific polyclonal rabbit anti-serum (1:500)(kindly provided by Dr. M. Pizza) diluted in PBS/BSA (PBS containing 3% bovine serum albumin (fraction V, Sigma)) for 1 h at room temperature. Cells were then washed with PBS, and incubated with FITC- or TRITC-labelled secondary antibodies directed against mouse or rabbit IgG (1:100)(Jackson Immuno Research Laboratories, West Grove). In some experiments, fixed cells were pre-treated with rhodamine-labelled wheat germ agglutinin (WGA, Sigma) to visualise plasma and Golgi membranes. Washed cover slips were then mounted onto glass examination slides spotted with Mowiol containing 2.5% 1,4-diazabicyclo[2.2.2]octane (DABCO) anti-fading and 4',6-diamidino-2-phenylindole dihydrochloride (DAPI)(1 mg/ml) for nuclear staining (all from Sigma), and then examined using a Leica DH1RBE inverted confocal microscope (Leica, Buffalo) at the MRC Cell Imaging Facility of the Department of Biochemistry, University Bristol.

Example 6

Epitope Attachment to EtxB (SEQ. ID NO: 15)

Based on our previous finding that the fusion to EtxB (SEQ. ID NO: 15) of a 27 amino acid, C-terminal peptide from the DNA polymerase (Pol) of HSV-1 enabled the peptide to be delivered into eukaryotic cells (14), it was decided to assess if the B-subunit could be used as a generic vehicle for delivery of epitopes into the class I presentation pathway. Since the Pol-peptide contained a number of features speculated to be involved in peptide liberation and endosomal translocation, namely a putative cathepsin D cleavage site (EKL.dwnarw.AG.dwnarw.F) and a loop segment of hydrophobic and charged amino acids (AGFGAVGAGATAEE) (SEQ ID NO: 11), these elements were incorporated adjacent to the well-characterised class I epitope (SIINFEKL) of ovalbumin. Thus, a 26-mer (SEQ. ID NO: 8) synthetic peptide was designed containing an N-terminal cysteine residue suitable for chemical conjugation, and the putative cleavage site, Pol-loop segment and model class I epitope (Table 1), and then chemically conjugated to EtxB (SEQ. ID NO: 15) as described in Materials & Methods.

Results 6

Figure 6A:
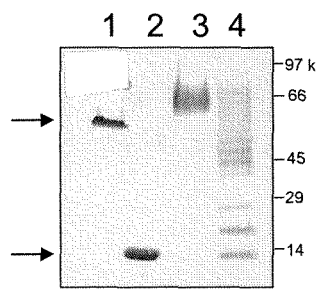
Figure 6B:
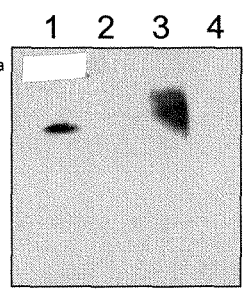
Figure 6C:
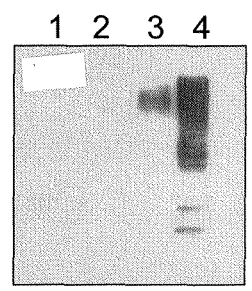
Figure 6D:
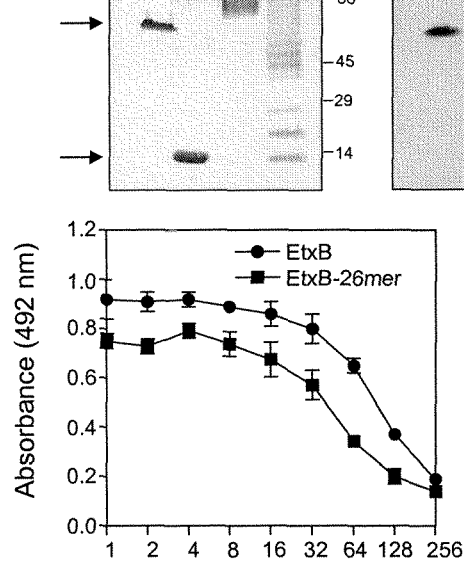
Figure 6E:
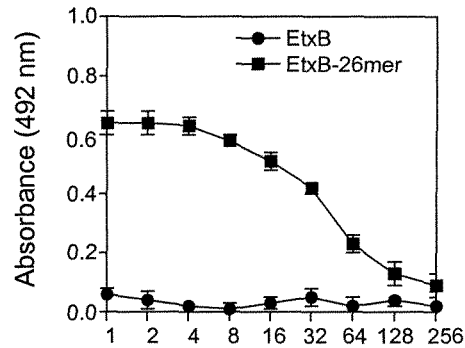

The resultant conjugate retained the characteristic stability properties of EtxB (SEQ. ID NO: 15), migrating as a pentameric high molecular weight species on SDS-polyacrylamide gels if kept unheated prior to analysis, and dissociating into monomers when boiled (FIG. 6A, lanes 3 and 4). The unheated conjugate had an electrophoretic mobility that was slower and had a more diffuse appearance than the native EtxB (SEQ. ID NO: 15) pentamer, suggestive of attachment of several 26-mer peptides (SEQ. ID NO: 8) per EtxB molecule (SEQ. ID NO: 15) (compare lanes 1 and 3). Upon boiling, monomeric conjugate species with one, two, or more conjugated peptides per EtxB (SEQ. ID NO: 15) monomer were evident (lane 4). Western blot analysis of EtxB (SEQ. ID NO: 15) and EtxB-26mer (SEQ. ID NO: 15-SEQ. ID NO: 8) conjugate demonstrated recognition of pentameric EtxB (SEQ. ID NO: 15) and EtxB-26mer (SEQ. ID NO: 15-SEQ. ID NO: 8) conjugate by a mAb 118-8, specific for the EtxB (SEQ. ID NO: 15) pentamer (FIG. 6B), and recognition of pentameric and monomeric EtxB-26mer (SEQ. ID NO: 15-SEQ. ID NO: 8) by a SIINFEKL-specific polyclonal antiserum (FIG. 6C). In GM1-binding ELISAs, the EtxB-26mer (SEQ. ID NO: 15-SEQ. ID NO: 8) conjugate could readily be detected with both EtxB (SEQ. ID NO: 15)- and SIINFEKL-specific antibodies, confirming its capacity to bind to GM1 (FIGS. 6D and E). The conjugate peptide:EtxB pentamer ratio, estimated by gel filtration chromatography, together with the conjugate concentration, was used to determine the apparent concentration of peptide in the conjugate as described in Materials & Methods.

Example 7

EtxB-26mer (SEQ. ID NO: 15-SEQ. ID NO: 8) Conjugate Efficiently Delivers SIINFEKL Peptide into the Class I Presentation Pathway The capacity of the EtxB-26mer (SEQ. ID NO: 15-SEQ. ID NO: 8) conjugate to deliver the OVA-derived SIINFEKL epitope into MHC-I was investigated in antigen presentation assays using JAWSII cells as antigen-presenting cells, and IL-2 release by the SIINFEKL-specific RF33.70 T-cell hybridoma as a read-out for antigen presentation.

Results 7

FIG. 7A shows that the EtxB-26mer (SEQ. ID NO: 15-SEQ. ID NO: 8) conjugate, but not peptide alone or EtxB (SEQ. ID NO: 15) admixed with peptide stimulated class I-restricted antigen presentation in a dose-dependent fashion. EtxB-mediated delivery reached plateau levels at the equivalent of 100 nM peptide, and IL-2 levels were comparable to those observed if cells were incubated with a free 8-mer SIINFEKL peptide (SEQ. ID NO: 4) (FIG. 7A). For a more direct assessment of antigen presentation, a FACS-based assay involving the use of mAb 25D1.16 specific for MHC-I/SIINFEKL complexes, was employed. The results obtained were in complete agreement with the IL-2 release data. Accordingly, the EtxB-26mer (SEQ. ID NO: 15-SEQ. ID NO: 8) conjugate and free SIINFEKL peptide (SEQ. ID NO: 4) induced a clear and similar shift in fluorescence (FIG. 7B), while EtxB (SEQ. ID NO: 15) and 26mer peptide (SEQ. ID NO: 8) alone or admixed failed to induce a shift in fluorescence (data not shown). This enhancement of antigen presentation was not due to EtxB-induced upregulation of MHC-I expression, as MHC-I expression levels remained unchanged after treatment with EtxB-conjugates (data not shown). Thus, the observed IL-2 release was the result of the appearance of MHC-I/SIEFEKL complexes on the cell surface and subsequent recognition and IL-2 production by the RF33.70 T cell hybridoma.

Example 8

Inclusion of Elements of the Pol Peptide Increase the Efficiency of EtxB-Mediated Class I Delivery In an attempt to confirm whether structural elements within the 26mer peptide (SEQ. ID NO: 8) were responsible for facilitating peptide delivery, 4 additional peptides, namely a 9mer, 16mer, 19mer (SEQ. ID NO: 7) and 26mer* (SEQ. ID NO: 9) were designed to address the contribution of the putative cleavage region and the Pol-loop segment (Table 1). All peptides were conjugated to EtxB (SEQ. ID NO: 15) and their ability to bind to GM1 was confirmed by GM1-sandwich ELISA as above (data not shown).

Results 8

Figures 8A, 8B:
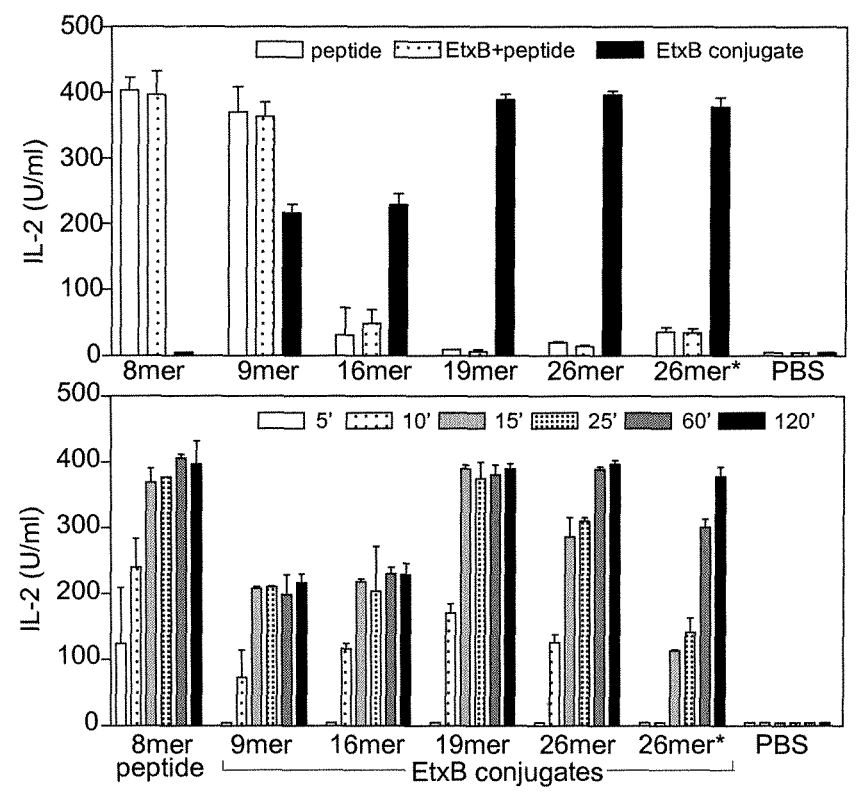

FIG. 8A shows that all of the EtxB-peptide conjugates, when used at 100 nM peptide equivalents, were able to trigger antigen presentation. Like the 8mer (SEQ. ID NO: 4), the 9mer CSIINFEKL peptide (SEQ. ID NO: 5), significantly stimulated class I presentation when tested alone or when admixed with EtxB (SEQ. ID NO: 15), indicating that it is capable of loading directly onto MHC-I molecules present on the cell surface. Interestingly, the extent of peptide delivery when the EtxB-9mer (SEQ. ID NO: 15-SEQ. ID NO: 5) was used was lower than for that achieved with the free 9mer peptide (SEQ. ID NO: 5) (FIG. 8A). The larger peptides could not load directly onto MHC-I, and were dependent on EtxB-mediated delivery for their presentation. The extent of EtxB-mediated delivery of the 16-mer peptide (SEQ. ID NO: 6), that contains the putative cleavage region adjacent to the SIINFEKL epitope, was very similar to that of the EtxB-9mer (SEQ. ID NO: 15-SEQ. ID NO: 5) conjugate. This indicates that the inclusion of the putative cathepsin D cleavage site does not contribute significantly to the extent of epitope delivery. By contrast, conjugation to EtxB (SEQ. ID NO: 15) of the 19mer (SEQ. ID NO: 7) and 26mer peptides (SEQ. ID NO: 8), which both contain the Pol-loop segment, resulted in increased peptide delivery, comparable to the maximal loading achieved with free 8mer SIINFEKL peptide (SEQ. ID NO: 4) (FIG. 8A). We therefore conclude that incorporation of the Pol-loop segment adjacent to the class I epitope causes a marked increase in the extent of EtxB-mediated epitope presentation.

To assess the kinetics of appearance of MHC-I/SIINFEKL complexes on the cell surface, cells were fixed at various time points after incubation with the EtxB-conjugates. After 5 min incubation with the conjugates no peptide presentation was evident, whilst after 15 min maximal presentation levels had been attained by all of the conjugates (FIG. 8B). As expected, addition of the free 8mer SIINFEKL peptide (SEQ. ID NO: 4), resulted in peptide presentation at the earliest time point tested.

To further investigate if the intrinsic properties of the Pol-loop segment contribute to peptide delivery, a 26mer* peptide (SEQ. ID NO: 9) was designed (Table 1). This contained a single Val to Arg substitution that should disrupt the relative hydrophobicity of the Pol-loop segment. When tested, the EtxB-26mer* (SEQ. ID NO: 15-SEQ. ID NO: 9) conjugate exhibited a marked alteration in kinetics of SIINFEKL epitope delivery with no presentation evident within the first 10 min, and only reaching maximal presentation after 120 min (FIG. 8B). Therefore, inclusion of the native Pol-loop segment (SEQ. ID NO: 11) appears to contribute to the efficiency of EtxB-mediated epitope delivery into the MHC-I presentation pathway.

Example 9(a)

Endosomal Acidification and an Intact Golgi are Required for EtxB-Mediated Epitope Delivery The trafficking pathway by which EtxB (SEQ. ID NO: 15) mediates the delivery of conjugated peptides into the MHC-I pathway was investigated using Bafilomycin A1 (BafA1), an inhibitor of the V-ATPase responsible for acidification of organelles of the endocytic pathway (18) and Brefeldin A (BFA), a Golgi-disrupting drug and inhibitor of vesicle-mediated secretion (19).

Results 9(a)

Treatment of JAWSII cells for 60 min with BafA1 or BFA, prior to addition of the EtxB-9mer (SEQ. ID NO: 15-SEQ. ID NO: 5), -16mer (-SEQ. ID NO: 6), -19mer (-SEQ. ID NO: 7), -26mer (-SEQ. ID NO: 8), and -26mer* (-SEQ. ID NO: 9) conjugates, led to complete inhibition of EtxB-mediated epitope delivery, as assessed using both the IL-2 release assay and FACS detection Of MHC-I/SIINFEKL complexes. Since the results obtained with all of the above conjugates were identical, only the data using the EtxB-19mer (SEQ. ID NO: 15-SEQ. ID NO: 7) are shown (FIGS. 9B-C & F-G). Importantly, treatment of JAWSII cells with BafA1 or BFA did not inhibit the direct loading and presentation of the free 8mer peptide (SEQ. ID NO: 4) (FIGS. 9B-C). Also, when monensin, a Na+-ionophor inhibitor of endosomal acidification was tested, EtxB-mediated epitope delivery was prevented, while presentation of the free 8mer peptide (SEQ. ID NO: 4) was unaffected (data not shown). Taken together these findings suggest that EtxB-mediated peptide presentation depends upon conjugate entry into acidic endosomes and targeting to the Golgi network.

Example 9(b)

Proteasome Involvement in EtxB-Mediated Epitope Presentation

To assess the possible requirement for proteasome-mediated processing of peptides delivered by EtxB (SEQ. ID NO: 15), the effect of well-characterised proteasome inhibitors was tested.

Results 9(b)

When epoxomicin, a specific proteasome inhibitor (20), was added to JAWSII cells 60 min prior to the addition of either EtxB-19mer (SEQ. ID NO: 15-SEQ. ID NO: 7) or free 8mer (SEQ. ID NO: 4), no inhibition of epitope presentation was observed (FIGS. 9D & H). Likewise, lactacysin and MG132, two additional inhibitors of proteasome activity, failed to prevent EtxB-mediated or free epitope presentation (data not shown). Similar results were obtained when all of the other EtxB peptide-conjugates were tested in the presence of epoxomicin, lactacysin or MG132 (data not shown). While such results are suggestive of a lack of proteasome involvement in the pathway of EtxB-mediated epitope delivery and presentation, Rock and colleagues have shown that proteasome cleavage of ovalbumin creates the proper C-terminus of the SIINFEKL epitope, whereas distinct peptidases in the cytosol or ER generate the appropriate N-terminus from extended peptides (21,22). Consequently, since all of the peptides we had tested contained the SIINFEKL epitope at their C-terminus, it is highly unlikely that the pathway of delivery of these epitopes would depend on proteasome-mediated cleavage. Therefore, in order to directly investigate if the proteasome could be a participant, a further 31 mer peptide (SEQ. ID NO: 10) was designed, comprising a five amino acid extension on the 26mer (SEQ. ID NO: 8), thus creating an internal SIINFEKL epitope (Table 1). Incubation of JAWSII cells with the EtxB-31mer (SEQ. ID NO: 15-SEQ. ID NO: 10) resulted in the efficient presentation of the SIINFEKL epitope, as assessed by the IL-2 release assay and by FACS (FIGS. 9A & E). As above, prior treatment with BafA1 or BFA prevented EtxB-31 mer (SEQ. ID NO: 15-SEQ. ID NO: 10) mediated epitope presentation (FIGS. 9B-C & F-G). However, in contrast to the behaviour of the other conjugates, epitope delivery by the EtxB-31mer (SEQ. ID NO: 15-SEQ. ID NO: 10) was completely blocked by the addition of epoxomicin (FIGS. 9D & H), lactacystin and MG132 (data not shown). This demonstrates that proteasome-mediated cleavage of the 31 mer peptide (SEQ. ID NO: 10) is necessary for it to enter the class I presentation pathway.

Example 10

EtxB-Conjugates Traffic to the Golgi where Newly Synthesised MHC-I Molecules are Loaded To visualise the trafficking pathway of the EtxB conjugates and to determine the localisation of MHC-I complexes, cells were treated with EtxB-19mer (SEQ. ID NO: 15-SEQ. ID NO: 7) or EtxB-31 mer (SEQ. ID NO: 15-SEQ. ID NO: 10), and stained with antibodies directed against EtxB (SEQ. ID NO: 15) or MHC-I/SIINFEKL and then examined by confocal microscopy.

Results 10

After 1 min of incubation with the conjugates, the EtxB (SEQ. ID NO: 15) moiety could be clearly seen at the cell surface while MHC-I/SIINFEKL complexes were undetectable (FIG. 10A, images e-h). After 120 min, both EtxB-19mer (SEQ. ID NO: 15-SEQ. ID NO: 7) and -31 mer (SEQ. ID NO: 15-SEQ. ID NO: 10) were almost completely internalised and perinuclear staining was evident with both EtxB- and MHC-I/SIINFEKL-specific antibodies, with considerable co-localisation (FIG. 10A, images i-1).

This perinuclear staining was suggestive of localisation of both EtxB (SEQ. ID NO: 15) and the MHC-I/SIINFEKL complexes in the ER or Golgi network, consistent with both the trafficking pathway of EtxB (SEQ. ID NO: 15) (23) and the normal cellular location of newly synthesised MHC-I molecules (6). In order to identify the cellular localisation of the MHC-I/SIINFEKL complexes more accurately, fixed cells were treated with rhodamine-labelled wheat germ agglutinin (WGA), specific for N-acetyl-β-D-acetylglucosamine present in Golgi/ER and plasma membranes (24), followed by anti-MHC-I/SIINFEKL and secondary antibodies (FIG. 10B). It was found that WGA and MHC-I/SIINFEKL complexes co-localised, confirming that these complexes were present in the Golgi (FIG. 10B, images a-d). Moreover, when cells were pre-incubated with epoxomicin to inhibit proteasome activity, no staining with MHC-I/SIINFEKL-specific antibodies was obtained when cells were treated with EtxB-31 mer (SEQ. ID NO: 15-SEQ. ID NO: 10) (FIG. 10B, images d vs h), whereas normal co-localisation of WGA and MHC-I/SIINFEKL complexes was observed when cells were treated with EtxB-19mer (SEQ. ID NO: 15-SEQ. ID NO: 7) (FIG. 10B, images c vs g). In addition, no detectable MHC-I/SIINFEKL complexes were observed when cells were treated with BafA1 or BFA, prior to addition of the EtxB-19mer (SEQ. ID NO: 15-SEQ. ID NO: 7) or EtxB-31mer (SEQ. ID NO: 15-SEQ. ID NO: 10) conjugates (data not shown). The above findings on the effects of the trafficking and proteasome inhibitors are in full agreement with the results obtained in the antigen presentation assays. We therefore conclude, that EtxB (SEQ. ID NO: 15) is an effective delivery vehicle capable of targeting attached epitopes from an exogenous location into the endogenous, proteasome-dependent, class I antigen processing and presentation pathway.

Example 11(a)

EtxB Mutants Retain their Targeting Potential Even Though they has Lost their Immunomodulatory Properties FIG. 11 shows a time course of entry of the EtxB(H57S) (SEQ. ID NO: 19) mutant into Jurkat T-cells in comparison with the wild-type B-subunit.

Results 11(a)

EtxB(H57S) (SEQ. ID NO: 19), like CtxB(H57A) (SEQ. ID NO: 13) described in Examples 1-5 above retains binding to GM1, but lacks the ability to trigger signalling events in leukocytes. As FIG. 11 shows, both wild-type EtxB (SEQ. ID NO: 15) and the mutant traffic into Jurkat T-cells with similar kinetics and cellular distribution. This the data that indicates that the mutants will retain their drug targeting potential even though they have lost their potent immunomodulatory properties

Example 12

EtxB(H57A) (SEQ. ID NO: 16) can be Used as a Peptide Delivery Vehicle

To establish that EtxB H57 mutants (SEQ. ID NOS: 16 & 19) retain their ability to serve as a peptide delivery vehicles, JAWS II cells were treated with an EtxB(H57A)-19mer (SEQ. ID NO: 15-SEQ. ID NO: 7) conjugate and epitope presentation evaluated as described in Example 7.

Results 12

FIG. 12 shows that the EtxB(H57A)-19mer (SEQ. ID NO: 15-SEQ. ID NO: 7) conjugate was able to stimulate class I-restricted antigen presentation at a level comparable to that achieved by the wild type EtxB-19mer (SEQ. ID NO: 15-SEQ. ID NO: 7) conjugate and by free 8mer SIINFEKL peptide (SEQ. ID NO: 4) that is capable of direct loading on MHC-I molecules present on the cell surface. Importantly, virtually no presentation occurred when either the free 19mer peptide (SEQ. ID NO: 7) or the 19mer peptide (SEQ. ID NO: 7) admixed with EtxB(H57A) (SEQ. ID NO: 16) was tested. Conjugation of the 19mer peptide (SEQ. ID NO: 7) to EtxB (G33D) (SEQ. ID NO: 14)—a non-binding mutant, also failed to lead to class I-restricted peptide presentation. We therefore conclude that EtxB(H57A) (SEQ. ID NO: 16) retains the delivery capabilities of the wild type EtxB molecule (SEQ. ID NO: 15).

SUMMARY

Part I

Examples 1-5 Mutants

GM-1 Binding and No Immodulation

To investigate whether this region of the B-subunits is important for toxin action in disease and in B-subunit-mediated immunomodulation, the individual residues of the loop were sequentially substituted for Ala Here we show that one of the mutants, with a His to Ala substitution at position 57 (CtxB(H57A) (SEQ. ID NO: 13)) is severely defective as an immunomodulator, and that the corresponding holotoxin, Ctx (H57A) (SEQ. ID NO: 13) exhibits ablated toxicity even though these molecules retain the ability to bind with high affinity to GM1. X-ray crystallographic analysis of CtxB (H57A) (SEQ. ID NO: 13) revealed that the loop region had undergone a striking 7 Å shift, partially occluding the pore region on the lower convoluted surface of the molecule, whilst not altering the capacity of the receptor pocket to co-crystallize with galactose. This indicates that the loop defies an important site on cholera toxin that is essential for its diverse activities, and that GM1-binding alone is not sufficient to trigger toxin action.

Part II

Example 6-12

Use of Wild Type (SEQ. ID NO: 15)/Mutant EtxB (SEQ. ID NOS: 14, 16, 19) to Deliver Exogenous Peptides into the Class I Antigen Processing and Presentation Pathways Here, we demonstrate that when a class I epitope is attached to EtxB (SEQ. ID NO: 15) or an EtxB (H57 mutant) (SEQ. ID NOS: 16 & 19), it can be delivered into the class I presentation pathway. Furthermore, we show that the efficiency of EtxB-mediated peptide delivery can be augmented by incorporating a 10 amino acid segment of the Pol-peptide adjacent to the class I epitope. Addition of a C-terminal extension to such epitope constructs led to class I presentation being completely dependent on proteasome activity. These findings, together with observations that presentation was dependent on endosomal acidification and an intact Golgi compartment, would indicate that EtxB (SEQ. ID NO: 15) and EtxB H57 mutants (SEQ. ID NOS: 16 & 19) are able to act as trafficking molecules that facilitates delivery of exogenous epitopes into the endogenous pathway of class I antigen processing and presentation.

Discussion (Part I)

GM 1-ganglioside receptor-binding by the B-subunit of cholera toxin (CtxB (SEQ. ID NO: 12)) is widely accepted to initiate toxin action, by triggering uptake and delivery of the toxin A-subunit into cells. More recently, GM1-binding by isolated CtxB (SEQ. ID NO: 12), or the related B-subunit of *E. coli* heat-labile enterotoxin (EtxB) has been found modulate leukocyte function, resulting in the down-regulation of proinflammatory immune responses that cause autoimmune disorders such as rheumatoid arthritis and diabetes.

The present invention demonstrates that GM1-binding, contrary to expectation, is not sufficient to initiate the potent toxic or immunomodulatory action of the toxin. Data from studies carried out on engineering and crystallographic structure of a mutant cholera toxin, with a His to Ala substitution in the B-subunit at position 57 demonstrated that the mutant retained pentameric stability and high affinity binding to GM1-ganglioside, but lost its immunomodulatory activity and, when part of the holotoxin complex, exhibited ablated toxicity.

Why does an H57A Mutation in CtxB (SEQ. ID NO: 12) Attenuate Ctx Action and Ablate B-Subunit-Mediated Immunomodulation?

It is possible that the H57A mutation subtly alters the nature of interaction with GM1 so that putative, and as yet ill-defined down-stream events cannot be activated. Previous crystallographic studies have revealed that the only structural change that occurs when B-pentamers interact with the pentasaccharide of GM1, or with other carbohydrates such as galactose, is that the loop region becomes more rigid (4). Whilst the significance of this has not been explored, it is possible that the transition from a flexible to a rigid structure contributes to the way in which bound GM1-moieties are tethered in the membrane. In this regard, the X-ray crystallography revealed that the loop of the H57A mutant receptor pocket, lacking bound carbohydrate, appeared to have already adopted a more rigid structure. This would therefore preclude the possibility of such a structural transition contributing to GM1-crosslinking in ways that may result in activation of down-stream events.

Alternatively, cholera toxin may require interaction, not only with GM1, but also with another cell surface molecule for it to exert its biological activity. It is conceivable that after binding to GM1, the loops in the B-pentamer are positioned to directly interact with other membrane components, possibly a transmembrane protein. Consequently, the alteration in the position of the loops in the B-subunit mutants may prevent this from happening, even though the molecule is tethered to the membrane via GM1. Importantly, GM1 is preferentially located in cholesterol-rich detergent-insoluble membrane microdomains, termed 'rafts', which contain numerous proteins involved in cell signalling (17). us, it is conceivable that wild type CtxB (SEQ. ID NO: 12) binding to GM1 in rafts positions it to interact with signalling molecules at the membrane surface that participate in toxin-mediated trafficking and immune cell modulation.

The data from the present invention provides evidence that the H57 mutation does not interfere with uptake or trafficking in a variety of cell types suggesting that the mutants are defective in signal transduction.

Discussion Part II

Example 6-11

Utility of Using Wild-Type EtxB (SEQ. ID NO: 15) and EtxB H57 Mutants (SEQ. ID NOS: 16 & 19) as Vehicle to Deliver Class I Epitopes Cytotoxic CD8+ T lymphocytes (CTL) represent an important component of the protective and therapeutic immune response to viral infections and tumours via their capacity to recognise foreign peptides that have bound to major histocompatibility complex class I (MHC-I) molecules (1,2). The majority of the peptides presented are derived from endogenously synthesised or cytoplasmically localised proteins that are cleaved into small peptide fragments by the proteasome (3,4). These are then transported via the transporter of antigenic peptides (TAP) into the lumen of the endoplasmatic reticulum (ER), where they bind to newly synthesised MHC-I molecules (5,6). Such MHC-I peptide complexes are trafficked to the cell surface whereupon they are recognised by T-cell receptors present on CTLs. This leads to CTL activation and subsequent CTL-mediated lysis of the peptide-presenting cell (1,2). Given the importance of CTLs in clearing the host of infected cells, there is a great interest in the development of new vaccination strategies that are capable of inducing effective CTL responses. However, for vaccines composed of soluble protein antigens, immunisation results in antigen uptake into an exogenous processing pathway that leads to peptide fragments being loaded onto MHC class II molecules (MHC-II), rather than MHC-I (7). Thus in order for soluble antigens to induce MHC-I restricted CTL responses, antigens need to access intracellular compartments where they can enter the endogenous class I processing and presentation pathway (7).

Bacterial protein toxins are molecules that combine unique cell-binding with efficient cytosolic delivery properties (8). They would therefore appear to be ideally suited for the delivery of antigenic proteins and peptides in the class I presentation pathway, provided that detoxification without apparent loss of delivery capability can be achieved. Indeed, toxoid derivatives of adenylate cyclase toxin of *Bordetella pertussis* (9), pertussis toxin (10), anthrax toxin (11,12), and Shiga toxin B subunit (13) have been investigated as potential vehicles for delivery of peptides or proteins into the class I presentation pathway. The non-toxic GM1-binding B-subunit of the *Escherichia coli* heat-labile enterotoxin (EtxB (SEQ. ID NO: 15)) has recently also been shown to be a suitable vehicle for the delivery of peptides into specific intracellular compartments (14). In particular, when a 27-mer peptide derived from the C-terminus of the DNA polymerase (Pol) of herpes simplex virus type 1 (HSV-1) was genetically fused to the C-terminus of EtxB (SEQ. ID NO: 15), it was found that the fusion protein entered cells, and that the peptide was liberated from EtxB (SEQ. ID NO: 15) and translocated into the nuclear compartment. While structural features present in the Pol-peptide were speculated to be involved in facilitating both its liberation from EtxB (SEQ. ID NO: 15) and translocation from endosomal compartments, their contribution to peptide delivery remained undefined. Here we have investigated: (i) whether EtxB (SEQ. ID NO: 15) (or mutant with an H57 mutation (SEQ. ID NOS: 16 & 19)) can be used as a vehicle for the delivery of exogenous peptides into the class I presentation pathway and (ii) whether incorporation of elements of the Pol-peptide adjacent to the class I epitope would improve the efficiency of peptide delivery.

We have shown that both EtxB (SEQ. ID NO: 15) and a mutant EtxB with a His to Ala substitution at residue 57 (SEQ. ID NO: 16) are effective vehicles for delivery of an epitope into the MHC-I pathway. The capacity of EtxB (SEQ. ID NO: 15) and EtxB (H57A) (SEQ. ID NO: 16) to bind to cells is essential for epitope delivery, since conjugates comprising peptides linked to a non-binding mutant of EtxB, EtxB(G33D) (25) (SEQ. ID NO: 14), failed to trigger peptide presentation. Given the finding that the proteasome can participate in the pathway of EtxB-mediated epitope presentation, it would imply that conjugated peptides are liberated from EtxB (SEQ. ID NO: 15) and translocated into the cytosol for proteasome processing.

Intrinsic properties of conjugated peptides were found to contribute to the extent and efficiency of epitope presentation. In this respect, conjugated peptides that were capable of achieving levels of presentation comparable to direct loading by the free SIINFEKL peptide (SEQ. ID NO: 4), all contained the Pol-loop segment, exemplified by the EtxB-19mer (SEQ. ID NO: 15-SEQ. ID NO: 7) conjugate. This segment was derived from a domain within the C-terminal region of HSV-1 polymerase and is part of a 36 amino acid hairpin-like structure, consisting of two helical regions interrupted by a flexible loop region that contains two glutamate residues (26,27). The Pol segment used in the current study contains the two glutamates and the flexible region composed of hydrophobic and nonpolar amino acids, and it shows a degree of similarity with fusion peptides from viral glycoproteins (28). Therefore, one explanation for the improved delivery of the SIINFEKL epitope by peptides containing the Pol-loop segment, may be that this segment has an intrinsic propensity to penetrate lipid bilayers. Furthermore, it is known that for pH-dependent translocation, protonation of acidic residues in helical hairpins permits insertion of hydrophobic domains into lipid bilayers (29). Thus, liberation from EtxB (SEQ. ID NO: 15), followed by protonation of the glutamates and then translocation across a vesicular membrane into the cytosol should permit highly efficient entry into the endogenous class I presentation pathway.

In support of this hypothesis, the mutated 26mer peptide, 26mer* (SEQ. ID NO: 9), with an Arg substitution in the middle of the Pol-loop segment, displayed slower delivery kinetics, possibly due to decreased translocation efficiency. Moreover, the finding that BafA1 and monensin inhibited EtxB-mediated epitope presentation indicates that entry into an acidic endosome is essential for peptide delivery. Given that the trafficking and toxicity of cholera toxin is refractory to chaotropic agents (30), this would imply that entry into an acidic environment is required for efficient epitope delivery rather than for trafficking of the carrier. Consequently, an acidic environment could enable protonation of the Pol-loop glutamate residues for subsequent translocation. It is also possible that entry into acidic endosomes is necessary for peptide liberation from EtxB (SEQ. ID NO: 15) as a result of the activity of acid-dependent proteases such as cathepsins. However, when EtxB-mediated presentation of the 26mer peptide (SEQ. ID. NO: 8) was assessed in the presence of pepstatin, an inhibitor of acid proteases, it had no effect on the extent of SIINFEKL presentation. In addition, there was no difference in the extent of epitope presentation mediated by EtxB-26mer (SEQ. ID NO: 15-SEQ. ID NO: 8), EtxB-19mer (SEQ. ID NO: 15-SEQ. ID NO: 7) and EtxB (H57A)-19mer (SEQ. ID NO: 16-SEQ. ID NO: 7) conjugates, the former of which lacks the putative cathepsin D cleavage sites. Inhibitors of metallo-aminopeptidases and serine and cysteine proteases, bestatin and leupeptin, also had no significant effects on EtxB-mediated epitope presentation. The metallo-protease inhibitor 1,10-phenanthroline was, however, found to inhibit EtxB-induced antigen presentation, suggesting that a metallo-protease may be involved in either liberation and/or processing of the EtxB-conjugated peptides.

The ability of EtxB (SEQ ID NO: 15) (and H57 mutants thereof (SEQ. ID NOS: 16 & 19)) and the Pol-loop segment to efficiently deliver class I restricted epitopes into the endogenous MHC-I pathway should open up new opportunities for design of vaccines able to stimulate protective cytotoxic T-cell responses. Given that the efficiency of CTL-mediated killing is directly related to the number of specific MHC-I peptide complexes on the cell surface (31), it is encouraging that the extent of peptide delivery mediated by EtxB (SEQ. ID NO: 15) reached comparable levels to direct loading of peptides onto surface MHC-I molecules.

A table of all Sequence ID Numbers and the corresponding sequences is submitted as Table 2.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

A table of all Sequence ID Numbers and the corresponding sequences is submitted as Table 2.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

REFERENCES (PART I)

Hirst, T. R. (1999) in The Comprehensive Sourcebook of Bacterial Protein Toxins, ed. Freer, J. E. A. a J. H. (Academic Press, London), pp. 104-129.

Lencer, W. I., Hirst, T. R & Holmes, R. K. (1999) Biochim. Biophys. Acta 1450, 177-190.

Holmgren, J., Lonnroth, I. & Svennerholm, L. (1973) Infect. Immun. 8, 208-214.

Sixma, T. K., Kalk, K H., van Zanten, B. A. M., Dauter, Z., Kingma, J., Witholt, B. & Hol, W. G. J. (1993) J. Mol. Biol. 230, 890-918.

Williams, N. A., Hirst, T. R. & Nashar, T. O. (1999) Immunol. Today 20, 95-101.

Verweij, W. R., de Haan, L., Holtrop, M., Agsteribbe, E., Brands, R., van Scharrenburg, G. J. M. & Wilschut, J. (1998) Vaccine 16, 2069-2076.

Richards, C. M., Aman, A. T., Hirst, T. R., Hill, T. J. & Williams, N. A. (2001) Journal of Virology 75, 1664-1671.

Sun, J. B., Rask, C., Olsson, T., Holmgren, J. & Czerkinsky, C. (1996) Proc. Natl. Acad. Sci. (USA) 93, 7196-7201.

Williams, N. A., Stasiuk, L. M., Nashar, T. O., Richards, C. M., Lang, A. K., Day, M. J. & Hirst, T. R. (1997) Proc. Natl. Acad. Sci. (USA) 94, 5290-5295.

Bergerot, I., Ploix, C., Petersen, J., Moulin, V., Rask, C., Fabien, N., Lindblad, M., Mayer, A., Czerkinsky, C., Holmgren, J. & Thivolet, C. (1997) Proc. Natl. Acad. Sci. (USA) 94, 4610-4614.

Francis, M. L., Ryan, J., Jobling, M. G., Holmes, R. K., Moss, J. & Mond, J. J. 1992) J. Immunol. 148, 1999-2005.

Nashar, T. O., Hirst, T. R. & Williams, N. A. (1997) Immunology 91, 572-578.

Nashar, T. O., Webb, H. M., Eaglestone, S., Williams, N. A. & Hirst, T. R. (1996) Proc. Natl. Acad. Sci. (USA) 93, 226-230.

Nashar, T. O., Williams, N. A. & Hirst, T. R. (1996) Int. Immunol. 8, 731-736.

Wolf, A. A., Jobling, M. G., Wimer-Mackin, S., Ferguson-Maltzman, M., Madara, J. L., Holmes, R. K. & Lencer, W. I. (1998) J. Cell Biol. 141, 917-927.

Orlandi, P. A. & Fishman, P. H. (1998) J. Cell Biol. 141, 905-915.

Parton, R. G., Joggerst, B. & Simons, K. (1994) J. Cell Biol. 127, 1199-1215.

Merritt, E. A., Sarfaty, S., van den Akker, F., Lhoir, C., Martial, J. A. & Hol, W. G. J. (1994) Protein Sci. 3, 166-175.

Merritt, E. A., Sixma, T. K., Kalk, K. H., Van Zanten, B. A. M. & Hol, W. G. J. (1994) Mol. Microbiol. 13, 745-753.

Higuchi, R., Krummel, B. & Saikid, R. K. (1988) Nucleic Acids Res. 16, 7351-7367.

Rodighiero, C., Aman, A. T., Kenny, M. J., Moss, J., Lencer, W. I. & Hirst, T. R. (1999) J. Biol. Chem. 274, 3962-3969.

Furste, J. P., Pansegrau, W., Frank, R., Blocker, H., Scholz, P., Bagdasarian, M. & Lanka, E. (1986) Gene 48, 119-131.

Hirst, T. R., Randall, L. L. & Hardy, S. J. S. (1984) Journal of Bacteriology 157, 637-642.

Ruddock, L. W., Ruston, S. P., Kelly, S. M., Price, N.C., Freedman, R1 B. & Hirst, T. R. (1995) J. Biol. Chem. 270, 29953-29958.

Merritt, E. A., Kuhn, P., Sarfaty, S., Erbe, J. L., Holmes, R. K & Ho, W. G. J. (1998) J. Mol. Biol. 282, 1043-1059.

Otwinowski, Z. & Minor, W. (1997) Meth. Enzymol. 276, 307-326.

Bailey, S. (1994) Acta Crystallogr. Sect. D-Biol. Crystallogr. 50, 760-763.

McRee, D. (1993) Practical Protein Crystallography (Academic Press, San Diego).

Sanner, M. F., Olson, A. J. & Spehner, J. C. (1996) Biopolymers 38, 305-320.

Merritt, E. A. & Bacon, D. J. (1997) Meth. Enzymol. 277, 505-524.

Lencer, W. I., Delp, C., Neutra, M. R. & Madara, J. L. (1992) J. Cell Biol. 117, 1197-1209.

Hardy, S. J. S., Holmgren, J., Johansson, S., Sanchez, J. & Hirst, T. R. (1988) Proc. Natl. Acad. Sci. (USA) 85, 7109-7113.

Sandkvist, M., Hirst, T. R. & Bagdasarian, M. (1990) J. Biol. Chem. 265, 15239-15244.

Kuziemko, G. M., Stroh, M. & Stevens, R. C. (1996) Biochemistry 35, 6375-6384.

Badizadegan, K., Wolf, A., Rodighiero, C., Jobling, M. G., Hirst, T. R., Holmes, R. K. & Lencer, W. I. (2000) Int. J. Med. Microbiol. 290, 403-408.

REFERENCES (PART II)

Townsend, A. & Bodmer, H. (1989) Annu. Rev. Immunol. 7, 601-624.

Long, E. O. & Jacobsen, S. (1989) Immunol. Today 10, 45-48.

Rock, K. L. & Goldberg, A. L. (1999) Annu. Rev. Immunol 17, 739-779.

Reits, E. A., Vos, J. C., Gromme, M. & Neefjes, J. (2000) Nature 404, 774-778.

Hill A. & Ploegh, H. (1995) Proc. Natl. Acad. Sci. USA 92, 341-343.

Heemels, M. T. & Ploegh, H. (1995) Annu. Rev. Biochem. 64, 463-491.

Raychaudhuri, S. & Rock, K. L. (1998) Nat. Biotechnol. 16, 1025-1031.

Burnette, W. N. (1994) Structure 2, 151-158.

Sebo, P., Fayolle, C., d'Andria, O., Ladant, D., Leclerc, C. & Ullmann, A. (1995) Infect Immum 63, 3851-3857.

Carbonetti, N. H., Irish, T. J., Chen, C. H., O'Connell, C. B., Hadley, G. A., McNamara, U., Tuskan, R. G. & Lewis, G. K (1999) Infect. Immun. 67, 602-607.

Ballard, J. D., Collier, R. J. & Starnbach, M. N. (1996) Proc. Natl. Acad. Sci. USA 93, 12531-12534.

Goletz, T. J., Klimpel, K. R., Arora, N., Leppla, S. H., Keith, J. M. & Berzofsky, J. A. (1997) Proc. Natl. Acad. Sci. USA 94, 12059-12064.

Lee, R. S., Tartour, E., van der Bruggen, P., Vantomme, V., Joyecux, I., Goud, B., Fridman, W. H. & Johannes, L. (1998) Eur. J. Immunol. 28, 2726-2737.

Loregian, A., Papini, E., Satin, B., Marsden, H. S., Hirst, T. R. & Palu, G. (1999) Proc. Natl. Acad. Sci. USA 96, 5221-5226.

Amin, T. & Hirst, T. R. (1994) Prot. Expr. Purif 5, 198-204.

Rock, K. L., Rothstein, L. & Gamble, S. (1990) J. Immunol. 145, 804-811.

Porgador, A., Yewdell, J. W., Deng, Y., Bennink, J. W. & Germain, R. N. (1997) Immunity 6, 715-726.

Bowman, E. J., Siebers, A. & Altendorf, K. (1988) Proc. Natl. Acad. Sci. USA 85, 7972-7976.

Lippincott-Schwartz, J., Yuan, L. C., Bonifacino, J. S. & Klausner, R. D. (1989) Cell 56, 801-813.

Meng, L., Mohan, R., Kwok, B. H., Elofsson, M., Sin, N. & Crews, C. M. (1999) Proc Natl. Acad. Sci. USA 96, 10403-10408.

Craiu, A., Akopian, T., Goldberg, A. & Rock, K. L. (1997) Proc. Natl. Acad. Sci. USA 94, 10850-10855.

Cascio, P., Hilton, C., Kisselev, A. F., Rock, K. L. & Goldberg, A. L. (2001) EMBO J. 20, 2357-2366.

Lencer, W. I., Delp, C., Neutra, M. R. & Madara, J. L. (1992) J. Cell Biol. 117, 1197-1209.

Tartakoff, A, M. & Vassalli, P. (1983) J. Cell Biol. 97, 1243-1248.

Nashar, T. O., Webb, H. M., Eaglestone, S., Williams, N. A. & Hirst, T. R (1996) Proc. Natl. Aca Sci. USA 93, 226-230.

Bridges, K. G., Hua, Q., Brigham-Burke, M. R., Martin, J. D., Hensley, P., Dahl, C. E., Digard, P., Weiss, M. A. & Coen, D. M. (2000) J. Biol. Chem. 275, 472-478.

Digard, P., Williams, K. P., Hensley, P., Brooks, I. S., Dahl, C. E. & Coen, D. M. (1995) Proc. Natl. Acad. Sci. USA 92, 1456-1460.

Samuel, O. & Shai, Y. (2001) Biochemistry 40, 1340-1349.

Kaul, P., Silverman, J., Shen, W. H., Blanke, S. R., Huynh, P. D., Finkelstein, A. & Collier, R. J. (1996) Prot. Sci. 5, 687-692.

Lencer, W. I., Strohmeier, G., Moe, S., Carlson, S. L., Constable, C. T. & Madara, J. L. (1995) Am. J. Physiol. 32, G548-G557.

Wherry, E. J., Puorro, K. A., Porgador, A. & Eisenlohr, L. C. (1999) J. Immunol. 163, 3735-3745.

---

What is claimed is:

1. A method of delivering a peptide to a MHC class I antigen processing pathway of an antigen presenting cell in a mammal, wherein the method comprises:
   providing an antigen presenting cell;
   contacting the cell with a mutant of E. coli heat labile enterotoxin B (EtxB; SEQ ID NO: 15) or Vibrio cholera cholera toxin B (CtxB; SEQ. ID NO. 12) covalently linked to the peptide, wherein said mutant comprises at least one of the following point mutations within a region spanning amino acid residues E51 to I58 of the β4-α2 loop of EtxB or CtxB: CtxB (E51A) (CtxB with E51A point mutation: SEQ ID NO: 17), CtxB (Q56A) (CtxB with Q56AA point mutation: SEQ ID NO: 18), CtxB (H57A) (CtxB with H57A point mutation: SEQ ID NO: 13), and EtxB (H57S) (EtxB with H57S point mutation: SEQ ID NO: 19), and has GM-1 binding activity, but reduced immunogenic and immunomodulatory activity relative to the corresponding wild type form of EtxB or CtxB.

2. The method of claim 1 wherein the mutant comprises a point mutation at H57A or H57S.

3. The method of claim 1, further comprising the step of monitoring the elicitation of a cytotoxic T lymphocyte (CTL) response in said mammal.

4. The method of claim 1 wherein the covalently linked peptide is derived from a protein of interest (POI) or an antigen.

5. The method of claim 4 wherein the antigen is selected from the group consisting of a viral antigen, a bacterial antigen, a parasitic antigen; and a tumor associated antigen (TAA).

6. The method of claim 1, further comprising monitoring peptide presentation by the MHC class 1 antigen processing pathway in the antigen presenting cell.

7. An in vivo method of delivering a peptide to a MHC class I antigen processing pathway of an antigen presenting cell in a mammal, wherein the method comprises:

contacting an antigen presenting cell in a mammal with a mutant of *E. coli* heat labile enterotoxin B (EtxB; SEQ ID NO: 15) or *Vibrio cholera* cholera toxin B (CtxB; SEQ. ID NO. 12) covalently linked to the peptide, wherein said mutant comprises at least one of the following point mutations within a region spanning amino acid residues E51 to I58 of the β4-α2 loop of EtxB or CtxB: CtxB (E51A) (CtxB with E51A point mutation: SEQ ID NO: 17), CtxB (Q56A) (CtxB with Q56AA point mutation: SEQ ID NO: 18), CtxB (H57A) (CtxB with H57A point mutation: SEQ ID NO: 13), and EtxB (H57S) (EtxB with H57S point mutation: SEQ ID NO: 19), and has GM-1 binding activity, but reduced immunogenic and immunomodulatory activity relative to the corresponding wild type form of EtxB or CtxB.

8. The method of claim 7 wherein the mutant comprises a point mutation at H57A or H57S.

9. The method of claim 7, further comprising the step of monitoring the elicitation of a cytotoxic T lymphocyte (CTL) response in said mammal.

10. The method of claim 7 wherein the covalently linked peptide is derivable derived from a protein of interest (POI) or an antigen.

11. The method of claim 10 wherein the antigen is selected from the group consisting of a viral antigen, a bacterial antigen, a parasitic antigen; and a tumor associated antigen (TAA).

12. The method of claim 7, further comprising monitoring peptide presentation by the MHC class 1 antigen processing pathway in the antigen presenting cell.

\* \* \* \* \*